US012595499B2

(12) United States Patent
Sugita

(10) Patent No.: US 12,595,499 B2
(45) Date of Patent: *Apr. 7, 2026

(54) PROTEIN HAVING 1,3-FUCOSYLTRANSFERASE ACTIVITY, AND METHOD FOR PRODUCING FUCOSE-CONTAINING SUGAR

(71) Applicant: PLUMINO PRECISION FERMENTATION JAPAN CO., LTD., Tokyo (JP)

(72) Inventor: Tomotoshi Sugita, Tokyo (JP)

(73) Assignee: Plumino Precision Fermentation Japan Co., Ltd., Tokyo (JP)

( * ) Notice: Subject to any disclaimer, the term of this patent is extended or adjusted under 35 U.S.C. 154(b) by 344 days.

This patent is subject to a terminal disclaimer.

(21) Appl. No.: 18/264,639

(22) PCT Filed: Feb. 8, 2022

(86) PCT No.: PCT/JP2022/004974
§ 371 (c)(1),
(2) Date: Aug. 8, 2023

(87) PCT Pub. No.: WO2022/168992
PCT Pub. Date: Aug. 11, 2022

(65) Prior Publication Data
US 2024/0301456 A1 Sep. 12, 2024

(30) Foreign Application Priority Data
Feb. 8, 2021 (JP) .................................. 2021-018483

(51) Int. Cl.
*C12P 19/18* (2006.01)
*C12N 9/10* (2006.01)
*C12R 1/19* (2006.01)

(52) U.S. Cl.
CPC ............ *C12P 19/18* (2013.01); *C12N 9/1051* (2013.01); *C12R 2001/19* (2021.05); *C12Y 204/01065* (2013.01)

(58) Field of Classification Search
CPC ........ C12P 19/18; C12P 19/00; C12N 9/1051; C12N 15/72; C12R 2001/19; C12Y 204/01065
See application file for complete search history.

(56) References Cited

U.S. PATENT DOCUMENTS

| | | | | |
|---|---|---|---|---|
| 9,441,211 | B2 * | 9/2016 | Parkot ................... | C12N 9/1051 |
| 10,336,990 | B2 | 7/2019 | Kim et al. | |
| 2006/0073542 | A1 | 4/2006 | Bayer et al. | |
| 2013/0217068 | A1 | 8/2013 | Parkot et al. | |
| 2017/0306373 | A1 | 10/2017 | Heidtman et al. | |
| 2019/0309336 | A1 | 10/2019 | Jennewein et al. | |
| 2024/0110212 | A1 * | 4/2024 | Sugita ................... | C12N 15/70 |

FOREIGN PATENT DOCUMENTS

| | | |
|---|---|---|
| EP | 2439264 A1 | 4/2012 |
| JP | 2013-541952 A | 11/2013 |
| JP | 6097691 B2 | 3/2017 |
| JP | 2017-527311 A | 9/2017 |
| JP | 2019-531752 A | 11/2019 |
| WO | 2016/040531 A1 | 3/2016 |
| WO | 2020/127417 A2 | 6/2020 |

OTHER PUBLICATIONS

Banerjee et al., Improving enzymes for biomass conversion: A basic research perspective. Bioenerg. Res., 2010, vol. 3: 82-92. (Year: 2010).*
Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Japan Patent Office, Written Opinion of the International Searching Authority in International Patent Application No. PCT/JP2022/004974 (Apr. 26, 2022).
Bych et al., "Production of HMOs using microbial hosts—from cell engineering to large scale production," *Curr. Opin. Biotechnol.*, 56: 130-137 (2019).

(Continued)

*Primary Examiner* — Ganapathirama Raghu
(74) *Attorney, Agent, or Firm* — Knobbe, Martens, Olson & Bear, LLP

(57) ABSTRACT

An object of the present invention is to provide a method for producing a fucose-containing carbohydrate more efficiently as compared with that in related art. The present invention relates to any one protein of [1] a protein consisting of the amino acid sequence represented by SEQ ID NO: 2 or 4, [2] a mutant protein having an α1,3-fucosyltransferase activity and consisting of an amino acid sequence in which 1 to 20 amino acids are deleted, substituted, inserted, or added in the amino acid sequence represented by SEQ ID NO: 2 or 4, and [3] a homologous protein having an α1,3-fucosyltransferase activity and consisting of an amino acid sequence having an identity of 90% or more with the amino acid sequence represented by SEQ ID NO: 2 or 4.

7 Claims, No Drawings
Specification includes a Sequence Listing.

(56)                    References Cited

OTHER PUBLICATIONS

Choi et al., "Solubilization and Iterative Saturation Mutagenesis of α1,3-Fucosyltransferase From *Helicobacter pylori* to Enhance Its Catalytic Efficiency," *Biotechnol. Bioeng.*, 113(8): 1666-1675 (2016).
Database UNIPROTKB, "Alpha-1,3-fucosyltransferase," Accession No. W4UPQ1 (uploaded Mar. 19, 2014) [obtained at https://www.uniprot.org/uniprot/W4UPQI on Apr. 13, 2022].
Huang et al., "Metabolic engineering of *Escherichia coli* for the production of 2'-fucosyllactose and 3-fucosyllactose through modular pathway enhancement," *Metab. Eng.*, 41: 23-38 (2017).
Lee et al., "Cloning and Functional Characterization of an α-1,3-fucosyltransferase from *Bacteroides fragilis*," *Biotechnol. Bioproc. Eng.*, 18: 843-849 (2013).

Ray et al., "Human Milk Oligosaccharides: The Journey Ahead," *Int. J. Pediatrics*, 2019: Article ID 2390240 (2019).
Yu et al., "Engineering of α-1,3-fucosyltransferases for production of 3-fucosyllactose in *Escherichia coli*," *Metab. Eng.*, 48: 269-278 (2018).
Japan Patent Office, International Search Report in International Patent Application No. PCT/JP2022/004974 (Apr. 26, 2022).
Yuki et al., "Draft Genome Sequence of Bacteroides reticulotermitis Strain JCM 10512T, Isolated from the Gut of a Termite," Genome Announc., 2(1): e00072-14 (2014).
European Patent Office, Extended European Search Report in European Patent Application No. 22749863.1 (Jun. 2, 2025).

\* cited by examiner

1

PROTEIN HAVING 1,3-FUCOSYLTRANSFERASE ACTIVITY, AND METHOD FOR PRODUCING FUCOSE-CONTAINING SUGAR

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 22,417 bytes ASCII (Text) file named "768068-Sequence Listing.txt," created Aug. 7, 2023.

TECHNICAL FIELD

The present invention relates to a protein having a 1,3-fucosyltransferase activity, and a method for producing a fucose-containing carbohydrate such as 3-fucosyllactose.

BACKGROUND ART

It has been reported that human milk oligosaccharides (HMO) contained in human milk have health functions such as improving the intestinal environment as a prebiotic, activating immunity, and developing cognitive functions in infants, and from a physiological activity thereof, they are expected to be used as an additive for infant formula and as a health functional ingredient for adults (Non Patent Literature 1).

Among carbohydrates known as HMOs, fucose-containing carbohydrates such as 3-fucosyllactose account for about 60% of the total HMOs in terms of substance amount ratio (Non Patent Literature 2), and among HMOs, particular attention is paid to functionality thereof.

As a method for producing 3-fucosyllactose, there is a method using a fucosyltransferase. Examples of the method for producing 3-fucosyllactose using a fucosyltransferase include a method using α1,3-fucosyltransferase derived from Helicobacter pylori (Non Patent Literature 3), or α1,3-fucosyltransferase derived from Bacteroides fragilis (Non Patent Literature 4 and Patent Literature 1). However, there is a problem that the activity of the fucosyltransferase is insufficient.

In order to solve the above problems, the effect of improving 3-fucosyllactose productivity is confirmed by, for example, modification of α1,3-fucosyltransferase derived from Helicobacter pylori, specifically, enzyme activity improvement by introduction of an amino acid mutation (Patent Literature 2 and Non Patent Literature 5), expression improvement by deletion or addition of a C-terminal amino acid sequence (Non Patent Literature 6), and the like.

CITATION LIST

Patent Literature

Patent Literature 1: Japanese Patent No. 6097691
Patent Literature 2: U.S. patent Ser. No. 10/336,990 specification

Non Patent Literature

Non Patent Literature 1: Int J Pediatrics (2019) 2390240: 1-8
Non Patent Literature 2: Curr Opin Biotechnol (2019) 56: 130-137

2

Non Patent Literature 3: Metabolic Engineering (2017) 41: 23-38
Non Patent Literature 4: Biotechnol Bioproc Eng (2013) 18: 843-849
Non Patent Literature 5: Biotechnol Bioeng (2016) 113: 1666-1675
Non Patent Literature 6: Metabolic Engineering (2018) 48: 269-278

SUMMARY OF INVENTION

Technical Problem

However, the effect of improving the 3-fucosyllactose productivity by the modification of α1,3-fucosyltransferase derived from Helicobacter pylori described in Patent Literature 2, Non Patent Literature 5, Non Patent Literature 6, and the like is insufficient, and a more efficient method for producing a fucose-containing carbohydrate is required.

Accordingly, an object of the present invention is to provide a method for producing a fucose-containing carbohydrate more efficiently as compared with that in related art.

Solution to Problem

The present inventor has found that 3-fucosyllactose can be efficiently produced by using a protein containing a specific amino acid sequence and having a 1,3-fucosyltransferase activity, as compared with that in related art, and has completed the present invention.

That is, the present invention is as follows.

1. A protein of any one of [1] to [3] below,
   [1] a protein consisting of the amino acid sequence represented by SEQ ID NO: 2 or 4,
   [2] a mutant protein having an α1,3-fucosyltransferase activity and consisting of an amino acid sequence in which 1 to 20 amino acids are deleted, substituted, inserted, or added in the amino acid sequence represented by SEQ ID NO: 2 or 4, and
   [3] a homologous protein having an α1,3-fucosyltransferase activity and consisting of an amino acid sequence having an identity of 90% or more with the amino acid sequence represented by SEQ ID NO: 2 or 4.

2. A DNA consisting of the nucleotide sequence represented by SEQ ID NO: 1 or 3 or a homologous sequence thereof and encoding the protein of any one of [1] to [3] according to the above 1.

3. A recombinant DNA comprising the DNA according to the above 2.

4. A transformant obtained by transforming a host cell with the recombinant DNA according to the above 3.

5. The transformant according to the above 4, which is a microorganism with an enhanced activity of the protein of any one of [1] to [3] according to the above 1 and enhanced fucose-containing carbohydrate productivity.

6. The transformant according to the above 5, in which the microorganism is Escherichia coli.

7. A method for producing a fucose-containing carbohydrate, including: culturing the transformant according to any one of the above 4 to 6 in a culture medium to produce a fucose-containing carbohydrate.

8. A method for producing a fucose-containing carbohydrate, including:
   culturing the transformant according to any one of the above 4 to 6 in a culture medium to obtain a culture product or a processed product of the culture product;

using the culture product or the processed product of the culture product as an enzyme source and causing the enzyme source, GDP-fucose, and a receptor carbohydrate to exist in an aqueous medium to produce a fucose-containing carbohydrate in the aqueous medium; and collecting the fucose-containing carbohydrate from the aqueous medium.

9. The method according to the above 7 or 8, in which the fucose-containing carbohydrate is 3-fucosyllactose.

Advantageous Effects of Invention

The protein of the present invention has an excellent α1,3-fucosyltransferase activity due to a specific amino acid sequence thereof. Therefore, by using the protein or a microorganism having an ability to produce the protein, a fucose-containing carbohydrate such as 3-fucosyllactose can be produced more efficiently as compared with that in related art.

DESCRIPTION OF EMBODIMENTS

1. Protein of Present Invention

A protein of the present invention is a protein according to any one of [1] to [3] below.

[1] a protein consisting of the amino acid sequence represented by SEQ ID NO: 2 or 4,

[2] a mutant protein having an α1,3-fucosyltransferase activity and consisting of an amino acid sequence in which 1 to 20 amino acids are deleted, substituted, inserted, or added in the amino acid sequence represented by SEQ ID NO: 2 or 4, and

[3] a homologous protein having an α1,3-fucosyltransferase activity and consisting of an amino acid sequence having an identity of 90% or more with the amino acid sequence represented by SEQ ID NO: 2 or 4.

A range of "1 to 20" in the "deletion, substitution, insertion, or addition of 1 to 20 amino acids" of the amino acid sequence is not particularly limited. For example, when 100 amino acids in the amino acid sequence are defined as one unit, the range of "1 to 20" per unit is 1, 2, 3, 4, 5, 6, 7, 8, 9, 10, 11, 12, 13, 14, 15, 16, 17, 18, 19, or 20, preferably about 1, 2, 3, 4, 5, 6, 7, 8, 9, or 10, and more preferably about 1, 2, 3, 4, or 5.

The expression "deletion of an amino acid" means deletion or elimination of an amino acid residue in a sequence, the expression "substitution of an amino acid" means substitution of an amino acid residue in a sequence with another amino acid residue, the expression "insertion of an amino acid" means insertion of a new amino acid residue in a sequence, and the expression "addition of an amino acid" means addition of a new amino acid residue so as to be inserted into a sequence.

As a specific embodiment of the "deletion, substitution, insertion, or addition of 1 to 20 amino acids", there is an embodiment in which 1 to 20 amino acids are substituted with other chemically similar amino acids. Examples thereof include a case where a certain hydrophobic amino acid is substituted with another hydrophobic amino acid, and a case where a certain polar amino acid is substituted with another polar amino acid having the same charge. Such chemically similar amino acids are known in the art for each amino acid.

Specific examples of the non-polar (hydrophobic) amino acid include alanine, valine, glycine, isoleucine, leucine, proline, tryptophan, phenylalanine, and methionine.

Examples of the polar (neutral) amino acid include serine, threonine, tyrosine, glutamine, asparagine, and cysteine. Examples of the positively charged basic amino acid include arginine, histidine, and lysine. Examples of the negatively charged acidic amino acid include aspartic acid and glutamic acid.

Examples of the amino acid sequence in which 1 to 20 amino acids are deleted, substituted, inserted, or added in an amino acid sequence of a target protein include an amino acid sequence having a sequence identity of a certain degree or more with the amino acid sequence of the target protein. Examples thereof include an amino acid sequence having an identity of preferably 60% or more, more preferably 65% or more, even more preferably 70% or more, still more preferably 75% or more, even still more preferably 80% or more, yet still more preferably 85% or more, further even still more preferably 90% or more, and particularly preferably 95% or more with the amino acid sequence of the target protein.

The fact that 1 to 20 amino acids are deleted, substituted, inserted, or added in the amino acid sequence represented by SEQ ID NO: 2 or 4 can be confirmed by, for example, aligning an amino acid sequence of a protein to be confirmed as having the deletion, substitution, insertion, or addition with an amino acid sequence of an original protein.

The alignment of the amino acid sequences can be created by using, for example, a well-known alignment program ClustalW [Nucelic Acids Research 22, 4673, (1994)]. ClustalW is available, for example, from http://www.ebi.ac.uk/clustalw/(European Bioinformatics Institute). For example, a default value can be used for parameters when creating an alignment using ClustalW.

When 1 to 20 amino acids are substituted, inserted, or added in the amino acid sequence represented by SEQ ID NO: 2 or 4, an amino acid residue to be substituted, inserted, or added may be natural or non-natural. Examples of the natural amino acid include L-alanine, L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, and L-cysteine.

Examples of mutually substitutable amino acids are shown below. Amino acids contained in the same group can be mutually substituted. Group A: leucine, isoleucine, norleucine, valine, norvaline, alanine, 2-aminobutanoic acid, methionine, o-methylserine, t-butylglycine, t-butylalanine, and cyclohexylalanine; Group B: aspartic acid, glutamic acid, isoaspartic acid, isoglutamic acid, 2-aminoadipic acid, and 2-aminosuberic acid; Group C: asparagine and glutamine; Group D: lysine, arginine, ornithine, 2,4-diaminobutanoic acid, and 2,3-diaminopropionic acid; Group E: proline, 3-hydroxyproline, and 4-hydroxyproline; Group F: serine, threonine, and homoserine; Group G: phenylalanine and tyrosine The α1,3-fucosyltransferase activity refers to an activity of transferring fucose from GDP-fucose, which is a donor substrate, to an N-acetyl glucosamine 3-hydroxyl group or a glucose 3-hydroxyl group of a carbohydrate (also referred to as a "receptor carbohydrate"), which is a receptor substrate, through α1,3-binding to produce a fucose-containing carbohydrate.

Examples of the receptor carbohydrate include N-acetylglucosamine, N-acetyllactosamine, galactose, fucose, sialic acid, glucose, or lactose, a combination thereof, and a glycan containing these as a partial structure. Among them, lactose is preferred.

Examples of the obtained fucose-containing carbohydrate include 3-fucosyllactose, lactodifucotetraose, Lewis X, and lacto-N-fucopentaose III. Among them, 3-fucosyllactose is preferred.

In the present description, the term "substrate" refers to substances on which α1,3-fucosyltransferase is capable of acting for producing a fucose-containing carbohydrate, or a combination thereof.

The mutant protein refers to a protein obtained by artificially deleting or substituting an amino acid residue of an original protein or artificially inserting or adding an amino acid residue in the protein. The expression an amino acid is deleted, substituted, inserted, or added in the mutant protein may mean that 1 to 20 amino acids are deleted, substituted, inserted, or added at any position in the same sequence.

An amino acid to be substituted, inserted, or added may be natural or non-natural. Examples of the natural amino acid include the above-described natural amino acids. Examples of mutually substitutable amino acids are as described above. Amino acids contained in the same group can be mutually substituted.

The homologous protein refers to a group of proteins derived from proteins of the same evolutionary origin, which are proteins possessed by organisms existing in nature. The homologous proteins are similar in structure and function to each other.

The identity of amino acid sequences and nucleotide sequences can be determined using an algorithm BLAST (Pro. Nat. Acad. Sci. USA, 90, 5873, 1993) or FASTA (Methods Enzymol., 183, 63, 1990) according to Karlin and Altschul. Based on the algorithm BLAST, a program called BLASTN or BLASTX has been developed (J. Mol. Biol., 215, 403, 1990). When analyzing a nucleotide sequence using BLASTN based on BLAST, parameters are, for example, Score=100 and wordlength=12. When analyzing an amino acid sequence using BLASTX based on BLAST, parameters are, for example, score=50 and wordlength=3. When using BLAST and Gap ped BLAST programs, use default parameters for each program. A specific method of the analysis method is known.

It can be confirmed by, for example, the following method that the above mutant protein or homologous protein has an α1,3-fucosyltransferase activity. First, a recombinant DNA comprising a DNA encoding the above mutant protein or homologous protein whose activity is to be confirmed is prepared by a method described later. Next, a microorganism obtained by transforming a microorganism having no α1,3-fucosyltransferase activity, for example, a *Escherichia coli* W3110 strain, with the recombinant DNA is cultured, and a cell extract containing the protein is prepared from the obtained culture product. The cell extract containing the protein is brought into contact with an aqueous solution containing GDP-fucose and a receptor carbohydrate as substrates to produce a fucose-containing carbohydrate in the aqueous solution. Finally, it can be confirmed that the mutant protein or homologous protein has an α1,3-fucosyltransferase activity by detecting the fucose-containing carbohydrate in a reaction liquid using a carbohydrate analyzer to be described later.

2. DNA of Present Invention

A DNA of the present invention is a DNA encoding the above protein according to any one of [1] to [3]. Specific examples of the DNA of the present invention include DNAs of [A1] to [A3] below.

[A 1] A DNA consisting of the nucleotide sequence represented by SEQ ID NO: 1 or 3.

[A2] A DNA hybridizing with a DNA consisting of a nucleotide sequence complementary to the nucleotide sequence represented by SEQ ID NO: 1 or 3 under stringent conditions and encoding a homologous protein having an α1,3-fucosyltransferase activity.

[A3] A DNA consisting of a nucleotide sequence having an identity of 95% or more, preferably 97% or more, more preferably 98% or more, and most preferably 99% or more with the nucleotide sequence represented by SEQ ID NO: 1 or 3 and encoding a homologous protein having an α1,3-fucosyltransferase activity.

In the above description, the term "hybridizing" refers to a step in which a DNA hybridizes to a DNA comprising a specific nucleotide sequence or a part of the DNA. Accordingly, a nucleotide sequence of the DNA hybridizing to a DNA comprising a specific nucleotide sequence or a part of the DNA may be useful as a probe for Northern or Southern blot analysis, or may be a DNA having a length that can be used as an oligonucleotide primer for PCR analysis.

Examples of the DNA used as a probe include DNAs having at least 100 bases or more, preferably 200 bases or more, and more preferably 500 bases or more. Examples of the DNA used as a primer include DNAs having at least 10 bases or more, and preferably bases or more.

A method for a DNA hybridization experiment is well known, and for example, Molecular Cloning, 4th Edition (Cold Spring Harbor Laboratory Press, 2012), Methods for General and Molecular Bacteriology (ASM Press, 1994), Immunology methods manual (Academic press, 1997), and many other standard textbooks can be followed to determine hybridization conditions and perform experiments.

The DNA hybridizing under stringent conditions can also be obtained by following an explanatory manual attached to a commercially available hybridization kit. Examples of the commercially available hybridization kit include a random primed DNA labeling kit (manufactured by Roche Diagnostics K.K.) in which a probe is prepared by a random prime method and hybridization is performed under stringent conditions.

Examples of the above stringent conditions include conditions where a filter on which a DNA is immobilized and a probe DNA are incubated overnight at 42° C. in a solution containing 50% formamide, 5×SSC (750 mM sodium chloride, 75 mM sodium citrate), 50 mM sodium phosphate (pH 7.6), a 5×Denhardt's solution, 10% dextran sulfate, and a 20 μg/L of denatured salmon sperm DNA, and then the filter is washed in a 0.2×SSC solution at, for example, about 65° C.

The above various conditions can also be set by adding or changing a blocking reagent used to reduce background in a hybridization experiment. The addition of the above blocking reagent may be accompanied by a change in hybridization conditions in order to meet the conditions.

Examples of the DNA capable of hybridizing under the above stringent conditions include a DNA consisting of a nucleotide sequence having an identity of 95% or more, preferably 97% or more, more preferably 98% or more, and most preferably 99% or more with the nucleotide sequence represented by SEQ ID NO: 1 or 3 when calculated based on the above parameters using the above program such as BLAST or FASTA.

The DNA of the present invention can be obtained by, for example, using a DNA encoding a protein consisting of the amino acid sequence represented by SEQ ID NO: 2 or 4, introducing a mutation by a site-directed mutagenesis method described in, for example, Molecular Cloning 4th Edition (Cold Spring Harbor Laboratory Press, 2012) and Current Protocols in Molecular Biology (JOHN WILEY &

SONS, INC.), and substituting with a nucleotide sequence encoding another amino acid residue. Alternatively, the DNA of the present invention can also be obtained by using a PrimeSTAR Mutagenesis Basal Kit (manufactured by Takara Bio Inc.), or the like.

The DNA encoding the protein consisting of the amino acid sequence represented by SEQ ID NO: 2 can be obtained by, for example, Southern hybridization to a chromosomal DNA library of a microorganism, preferably of the genus *Bacteroides* microorganism, and more preferably of a *Bacteroides* reticulotermitis JCM10512 strain using a probe that can be designed based on the nucleotide sequence of the DNA encoding the protein comprising the amino acid sequence represented by SEQ ID NO: 2, or by PCR [PCR Protocols, Academic press (1990)] using a primer DNA that can be designed based on the DNA encoding the protein consisting of the amino acid sequence represented by SEQ ID NO: 2 and using, as a template, a chromosomal DNA of a *Bacteroides* reticulotermitis JCM10512 strain. Specific examples of the DNA encoding the protein consisting of the amino acid sequence represented by SEQ ID NO: 2 include a DNA comprising the nucleotide sequence represented by SEQ ID NO: 1.

The DNA encoding the amino acid sequence represented by SEQ ID NO: 4 can be obtained by, for example, chimerization by fusion PCR shown in the following (i) or (ii).

(i) Chimerization, by fusion PCR, of the following three DNA fragments (i-1) to (i-3) obtained by Southern hybridization to each chromosomal DNA library using a probe that can be designed based on the nucleotide sequence of the DNA encoding the protein consisting of the amino acid sequence represented by SEQ ID NO: 4

(i-1) A DNA fragment consisting of the nucleotide sequence at positions 1 to 342 in the nucleotide sequence represented by SEQ ID NO: 3, which is obtained by Southern hybridization to a chromosomal DNA library of a microorganism, preferably of the genus *Bacteroides* microorganism, and more preferably of a *Bacteroides* reticulotermitis JCM 10512 strain (i-2) A DNA fragment consisting of the nucleotide sequence at positions 607 to 954 in the nucleotide sequence represented by SEQ ID NO: 3, which is obtained by Southern hybridization to a chromosomal DNA library of a microorganism, preferably of the genus *Bacteroides* microorganism, and more preferably of a *Bacteroides* reticulotermitis JCM 10512 strain (i-3) A DNA fragment consisting of a nucleotide sequence obtained by codon-optimizing, for expression in *Escherichia coli*, a nucleotide sequence encoding the amino acid sequence at positions 127 to 214 in the amino acid sequence represented by SEQ ID NO: 6 which is obtained by Southern hybridization to a chromosomal DNA library of a *Bacteroides fragilis* ATCC25285 strain (ii) Chimerization, by fusion PCR, of the following three DNA fragments ((ii-1) to ((ii-3) obtained by PCR using a primer DNA that can be designed based on a DNA encoding the protein consisting of the amino acid sequence represented by SEQ ID NO: 4 and using each chromosomal DNA as a template (ii-1) A DNA fragment consisting of the nucleotide sequence at positions 1 to 342 in the nucleotide sequence represented by SEQ ID NO: 3, which is obtained by PCR using, as a template, a chromosomal DNA of a microorganism, preferably of the genus

*Bacteroides* microorganism, and more preferably of a *Bacteroides* reticulotermitis JCM 10512 strain (ii-2) A DNA fragment consisting of the nucleotide sequence at positions 607 to 954 in the nucleotide sequence represented by SEQ ID NO: 3, which is obtained by PCR using, as a template, a chromosomal DNA of a microorganism, preferably of the genus *Bacteroides* microorganism, and more preferably of a *Bacteroides* reticulotermitis JCM 10512 strain (ii-3) A DNA fragment consisting of the nucleotide sequence obtained by codon-optimizing, for expression in *Escherichia coli*, a nucleotide sequence encoding the amino acid sequence at positions 127 to 214 in the amino acid sequence represented by SEQ ID NO: 6, which is obtained by PCR using, as a template, a chromosomal DNA of a *Bacteroides fragilis* ATCC25285 strain Specific examples of the DNA encoding the protein consisting of the amino acid sequence represented by SEQ ID NO: 4 include a DNA comprising the nucleotide sequence represented by SEQ ID NO: 3.

A DNA encoding the mutant protein having a 1,3-fucosyltransferase activity and consisting of an amino acid sequence in which 1 to 20 amino acids are deleted, substituted, inserted, or added in the amino acid sequence represented by SEQ ID NO: 2 or 4 according to the above [2] can be obtained by, for example, subjecting the DNA consisting of the nucleotide sequence represented by SEQ ID NO: 1 or 3 to error-prone PCR or the like as a template.

Alternatively, the DNA encoding the mutant protein having a 1,3-fucosyltransferase activity and consisting of an amino acid sequence in which 1 to 20 amino acids are deleted, substituted, inserted, or added in the amino acid sequence represented by SEQ ID NO: 2 or 4 according to the above [2] can also be obtained by a partially directed mutagenesis method by PCR using a set of PCR primers each having a nucleotide sequence designed to introduce a desired mutation (deletion, substitution, insertion, or addition) at the 5' end (Gene, 77, 51, 1989).

The DNA can also be obtained by following an explanatory manual attached to a commercially available partially directed mutagenesis kit. Examples of the commercially available partially directed mutagenesis kit include a Prime-STAR (registered trademark) Mutagenesis Basal Kit (manufactured by Takara Bio Inc.) capable of introducing a mutation (deletion, substitution, insertion, or addition) at a position to which a desired mutation is to be introduced.

That is, first, a pair of mutagenesis primers having a 15-base overlap on the 5' side is designed using a plasmid comprising a nucleotide sequence designed to introduce a desired mutation (deletion, substitution, insertion, or addition) as a template. At this time, the overlap portion includes a desired mutation. Next, PCR is performed using the mutagenesis primers and using a plasmid comprising a nucleotide sequence into which a desired mutation is introduced as a template. When the amplified fragment thus obtained is transformed into *Escherichia coli*, a plasmid comprising a nucleotide sequence into which a desired mutation is introduced is obtained.

The DNA encoding the homologous protein having an α1,3-fucosyltransferase activity and consisting of an amino acid sequence having an identity of 90% or more with the amino acid sequence represented by SEQ ID NO: 2 or 4 can be obtained by, for example, the following method. Specifically, for example, the DNA encoding the homologous protein can be obtained by a method similar to the method for obtaining the DNA encoding the protein consisting of the amino acid sequence represented by SEQ ID NO:2 or 4, using a probe DNA or primer DNA that can be designed based on a nucleotide sequence or an amino acid sequence obtained by searching various gene sequence databases for a nucleotide sequence having an identity of preferably 80% or more, more preferably 90% or more, even more preferably 95% or more, and most preferably 99% or more with the nucleotide sequence represented by SEQ ID NO: 1 or 3, and a microorganism having the DNA.

The identity of the nucleotide sequence and the amino acid sequence can be determined by a method same as that described in the above 1. A nucleotide sequence of the DNA of the present invention obtained by the above method can be determined by using the DNA as it is or cleaving the DNA with an appropriate restriction enzyme or the like, incorporating the DNA into a vector by an ordinary method, introducing the obtained recombinant DNA into a host cell, and then analyzing the DNA using a nucleotide sequence analysis method generally used, such as a dideoxy method (Proc. Nat. Acad. Sci., USA, 74, 5463, 1977) or a nucleotide sequence analyzer such as an Applied Biosystems 3500 Genetic Analyzer and an Applied Biosystems 3730 DNA Analyzer (both manufactured by Thermo Fisher Scientific K.K.).

Examples of the vector that can be used for determining the nucleotide sequence of the DNA of the present invention include pBluescriptII KS(+) and pPCR-Script Amp SK(+) (both manufactured by Agilent Technologies, Inc.), pT7Blue (manufactured by Merck Millipore Inc.), pCRII (manufactured by Thermo Fisher Scientific K.K.), pCR-TRAP (manufactured by Gene Hunter), and pDIRECT (Nucleic Acids Res., 18, 6069, 1990).

The above host cell may be any cell as long as the vector can be introduced and proliferated, and examples thereof include Escherichia coli DH5a, Escherichia coli HST08 Premium, Escherichia coli HST02, Escherichia coli HST04 dam-/dcm-, Escherichia coli JM109, Escherichia coli HB101, Escherichia coli CJ236, Escherichia coli BMH71-18 mutS, Escherichia coli MV1184, and Escherichia coli TH2 (all manufactured by Takara Bio Inc.), Escherichia coli XL1-Blue and Escherichia coli XL2-Blue (both manufactured by Agilent Technologies, Inc.), Escherichia coli DH1, Escherichia coli MC1000, Escherichia coli W1485, Escherichia coli W3110, Escherichia coli MP347, and Escherichia coli NM522.

As a method for introducing the recombinant DNA obtained by incorporating the DNA of the present invention into a host cell, any method for introducing a DNA into a host cell can be used, and examples thereof include a method using calcium ions (Proc. Natl. Acad. Sci., USA, 69, 2110, 1972), a protoplast method (JPS63-248394A), and an electroporation method (Nucleic Acids Res., 16, 6127, 1988).

When the obtained DNA is partial length as a result of determining the nucleotide sequence, the full-length DNA can be obtained by a Southern hybridization method or the like for a chromosomal DNA library using the partial length DNA as a probe.

Further, a target DNA can also be prepared by chemical synthesis using an NTS M series DNA synthesizer or the like manufactured by Nihon Techno Service Co., Ltd. based on the determined DNA nucleotide sequence.

3. Recombinant DNA of Present Invention

A recombinant DNA of the present invention is a DNA autonomously replicatable in a host cell, and is obtained by incorporating the DNA of the present invention of the above 2 into an expression vector comprising a promoter at a position where the DNA of the present invention can be transcribed.

A DNA capable of being incorporated into a chromosome in a host cell and comprising the DNA of the present invention is also the recombinant DNA of the present invention. When the recombinant DNA is a recombinant DNA capable of being incorporated into a chromosome, the recombinant DNA may not contain a promoter.

When a prokaryote such as bacteria is used as a host cell, the recombinant DNA of the present invention is preferably a recombinant DNA composed of a promoter, a ribosomal binding sequence, the DNA of the present invention of the above 2, and a transcription termination sequence. Further, a gene controlling a promoter may be comprised.

Here, it is preferred to adjust a distance between a shine-dalgarno sequence, which is a ribosomal binding sequence, and an initiation codon to an appropriate distance, for example, 6 to 18 bases. In the recombinant DNA of the present invention, the transcription termination sequence is not necessarily required for the expression of the DNA of the present invention, but it is preferred to place a transcription termination sequence immediately below the structural gene.

When a microorganism belonging to the genus Escherichia is used as a host cell into which the recombinant DNA of the present invention is to be introduced, examples of the expression vector include pColdI, pSTV28, and pUC118 (all manufactured by Takara Bio Inc.), pET21a, pCDF-1b, and pRSF-1b (all manufactured by Merck Millipore Inc.), pMAL-c5x (manufactured by New England Biolabs), pGEX-4T-1 and pTrc99A (both manufactured by GE Healthcare Bioscience), pTrcHis and pSE280 (both manufactured by Thermo Fisher Scientific K.K.), pGEMEX-1 (manufactured by Promega Corporation), pQE-30, pQE-60, and pQE80L (all manufactured by Qiagen), pET-3, pBluescriptII SK(+), and pBluescriptII KS(−) (all manufactured by Agilent Technologies, Inc.), pKYP10 (JPS58-110600A), pKYP200 (Agric. Biol. Chem., 48, 669, 1984), pLSA1 (Agric. Biol. Chem., 53, 277, 1989), pGEL1 (Proc. Natl. Acad. Sci., USA, 82, 4306 (1985), pTrS30 [prepared from Escherichia coli JM109/pTrS30 (FERM BP-5407)], pTrS32 [prepared from Escherichia coli JM109/pTrS32 (FERM BP-5408)], pTK31 [APPLIED AND ENVIRONMENTAL MICROBIOLOGY, 2007, Vol. 73, No. 20, p6378-6385], pPE167 (Appl. Environ. Microbiol. 2007, 73: 6378-6385), pPAC31 (WO 1998/12343), pUC19 (Gene, 33, 103, 1985), and pPA1 (JPS63-233798A).

The promoter in the case of using the above expression vector may be any promoter as long as it functions in cells of a microorganism belonging to the genus Escherichia, and examples thereof include a promoter derived from Escherichia coli, phage, or the like, such as a trp promoter, a gapA promoter, a lac promoter, a PL promoter, a PR promoter, or a PSE promoter. Examples thereof include a promoter which is artificially modified in design, such as a promoter with two promoters in series, a tac promoter, a trc promoter, a lacT5 promoter, a lacT7 promoter, or a letI promoter.

When a coryneform bacterium is used as a host cell into which the recombinant DNA of the present invention is to be introduced, examples of the expression vector include pCG1 (JPS57-134500A), pCG2 (JPS58-35197A), pCG4 (JPS57-183799A), pCG11 (JPS57-134500A), pCG 116, pCE54, and pCB101 (all JPS58-105999A), pCE51, pCE52, and pCE53 (all Molecular and General Genetics, 196, 175, 1984).

When the above expression vector is used, the promoter may be any promoter as long as it functions in cells of the coryneform bacterium, and examples thereof include a P54-6 promoter (Appl. Microbiol. Biotechnol., 53, p674-679, 2000).

When a yeast strain is used as a host cell into which the recombinant DNA of the present invention is to be introduced, examples of the expression vector include YEp13 (ATCC 37115), YEp24 (ATCC 37051), YCp50 (ATCC 37419), pHS19, and pHS15.

The promoter in the case of using the above expression vector may be any promoter as long as it functions in cells of the yeast strain, and examples thereof include a PHO5 promoter, a PGK promoter, a GAP promoter, an ADH promoter, a gal1 promoter, a gal10 promoter, a heat shock polypeptide promoter, an MFα1 promoter, and a CUP1 promoter.

The recombinant DNA of the present invention can be prepared by, for example, subjecting the DNA fragment prepared by the method of the above 2 to a restriction enzyme treatment or the like and inserting the DNA fragment into downstream of the promoter of the appropriate expression vector.

Here, by substituting a nucleotide such that the nucleotide sequence constituting the DNA of the present invention is an optimal codon for expression in a host cell, the expression level of the protein encoded by the DNA can be improved. Information on the frequency of codon use in a host cell can be obtained through a public database.

4. Transformant of Present Invention

A transformant of the present invention is a transformant obtained by transforming a host cell with the recombinant DNA comprising the DNA of the present invention according to the above 2. In the present description, the term "host cell" refers to an original cell to be transformed by gene transfer.

Specific examples of the transformant of the present invention include a microorganism with an enhanced activity of the protein of any one of above [1] to [3] and enhanced fucose-containing carbohydrate productivity. Examples thereof include a microorganism with enhanced fucose-containing carbohydrate productivity as compared with a parent strain, which is obtained by transforming the parent strain with the recombinant DNA comprising the DNA of any one of above [A1] to [A3]. In the present description, the term "parent strain" refers to an original strain to be subjected to genetic modification, transformation, and the like.

Examples of the microorganism with enhanced fucose-containing carbohydrate productivity as compared with a parent strain, which is obtained by transforming the parent strain with the recombinant DNA include the following microorganisms i) to iii).

i) A microorganism in which a transcription amount of the DNA or a production amount of the protein encoded by the DNA is increased by introducing the recombinant DNA comprising any one of the DNAs of above [A1] to [A3] into a parent strain as an autonomously replicable plasmid or by incorporating the recombinant DNA into a chromosome of a parent strain ii) A microorganism in which fucose-containing carbohydrate productivity is enhanced by producing a protein having an α1,3-fucosyltransferase activity with an enhanced specific activity as the mutant protein of the above [2]

iii) A microorganism in which fucose-containing carbohydrate productivity is enhanced by producing a protein having an α1,3-fucosyltransferase activity with enhanced specific activity as the homologous protein of the above [3]

As a method for confirming that the transcription amount of the DNA according to any one of above [A1] to [A3] or the production amount of the protein encoded by the DNA is increased, for example, it can be confirmed by measuring the transcription amount of the DNA by Northern blotting or the production amount of the protein by Western blotting, and comparing the transcription amount of the DNA or the production amount of the protein with that of a parent strain.

As a method for confirming that the specific activity of the protein having an α1,3-fucosyltransferase activity is enhanced, for example, it can be confirmed by purifying a mutant protein from a transformed strain obtained by transforming a parent strain with a DNA encoding the mutant protein, causing the protein, GDP-fucose, and a receptor carbohydrate to exist in an aqueous medium, measuring a specific activity from the amounts of the fucose-containing carbohydrate and the protein produced and accumulated in the aqueous medium, and comparing the specific activity with a specific activity of a protein having a fucose-containing carbohydrate producing activity and having no mutation introduced therein, which is measured in the same manner.

Examples of such a transformant of the present invention include a T166/pATY2 strain and a T166/pATY3 strain to be described later in Examples.

The host cell into which the recombinant DNA of the present invention is to be introduced may be any of a prokaryote, a yeast, an animal cell, an insect cell, a plant cell, and the like. The host cell is preferably a prokaryote or a yeast strain, is more preferably a prokaryote belonging to the genus *Escherichia*, the genus *Serratia*, the genus *Bacillus*, the genus *Brevibacterium*, the genus *Corynebacterium*, the genus *Microbacterium*, the genus *Pseudomonas*, or the like, or a yeast strain belonging to the genus *Saccharomyces*, the genus *Schizosaccharomyces*, the genus *Kluyveromyces*, the genus *Trichosporon*, the genus Siwaniomyces, the genus *Pichia*, the genus *Candida*, or the like, and is most preferably a prokaryote such as *Escherichia coli* [e.g., *Escherichia coli* BL21 codon plus, *Escherichia coli* XL1-Blue, and *Escherichia coli* XL2-Blue (all manufactured by Agilent Technologies, Inc.), *Escherichia coli* BL21 (DE3) pLysS (manufactured by Merck Millipore Inc.), *Escherichia coli* DH5a, *Escherichia coli* HST08 Premium, *Escherichia coli* HST02, *Escherichia coli* HST04 dam⁻/dcm⁻, *Escherichia coli* JM109, *Escherichia coli* HB101, *Escherichia coli* CJ236, *Escherichia coli* BMH71-18 mutS, *Escherichia coli* MV1184, and *Escherichia coli* TH2 (all manufactured by Takara Bio Inc.), *Escherichia coli* W, *Escherichia coli* JM101, *Escherichia coli* W3110, *Escherichia coli* MG1655, *Escherichia coli* DH1, *Escherichia coli* MC1000, *Escherichia coli* W1485, *Escherichia coli* MP347, *Escherichia coli* NM522, *Escherichia coli* ATCC 9637, *Serratia ficaria*, *Serratia fonticola*, *Serratia liquefaciens*, *Serratia marcescens*, *Bacillus subtilis*, *Bacillus amyloliquefaciens*, *Brevibacterium* immariophilum [for example, *Brevibacterium immariophilum* ATCC 14068], *Brevibacterium saccharolyticum* [e.g., *Brevibacterium saccharolyticum* ATCC 14066], *Corynebacterium ammoniagenes*, *Corynebacterium glutamicum* [*Corynebacterium glutamicum* ATCC 13032, *Corynebacterium glutamicum* ATCC 14067, *Corynebacterium glutamicum* ATCC 13869], *Corynebacterium acetoacidophilum* [*Corynebacterium* acetoa cidophilum ATCC 13870], *Microbacterium* ammoniaphilum [*Microbacterium* ammoniaphilum ATCC 15354], or *Pseudomonas* (for example, *Pseudomonas* sp. D-0110), or a yeast strain such as *Saccharomyces cerevisiae*, *Schizosaccharomyces pombe*,

*Kluyveromyces lactis, Trichosporon pullulans, Schwannio-myces alluvius, Pichia pastoris*, or *Candida utilis*.

Examples of the host cell include the following 1) and 2).

1) A microorganism used as a host cell that is artificially endowed or enhanced with an ability to produce GDP-fucose, which is a reaction substrate for a fucosyltransferase 2) A microorganism used as a host cell that is artificially endowed or enhanced with an ability to supply a receptor carbohydrate, which is a reaction substrate for a fucosyltransferase Hereinafter, each host cell will be described.

1) A microorganism used as a host cell that is artificially endowed or enhanced with an ability to produce GDP-fucose, which is a reaction substrate for a fucosyltransferase The host cell is preferably a microorganism that is artificially endowed or enhanced with an ability to produce GDP-fucose, which is a reaction substrate of α1,3-fucosyltransferase. Specific examples of a method for endowing or enhancing the ability to produce GDP-fucose to a microorganism used as a host cell include a known method such as a method using various genetic manipulations (Metabolic Engineering (2017) 41: 23-38).

Examples of the ability to produce GDP-fucose include an ability to produce GDP-fucose from a saccharide. Examples of the method for artificially endowing or enhancing the ability to produce GDP-fucose from a saccharide to a microorganism used as a host cell include the following methods (1a) to (1d). These methods may be used alone or in combination.

(1a) A method of alleviating or releasing at least one mechanism for controlling a biosynthetic pathway for producing GDP-fucose from a saccharide (1b) A method of enhancing expression of at least one enzyme associated with a biosynthetic pathway for producing GDP-fucose from a saccharide (1c) A method of increasing the number of copies of at least one gene encoding an enzyme associated with a biosynthetic pathway for producing GDP-fucose from a saccharide (1d) A method of weakening or blocking at least one metabolic pathway branching off from a biosynthetic pathway for producing GDP-fucose from a saccharide to a metabolic product other than a target substance Specific examples of the mechanism for controlling a biosynthetic pathway for producing GDP-fucose from a saccharide include known mechanisms such as a control mechanism based on a transcription control factor (e.g., RcsA) associated with control of the biosynthetic pathway.

Specific examples of the enzyme associated with the biosynthetic pathway for producing GDP-fucose from a saccharide include known enzymes such as a mannose-6-phosphate isomerase, a phosphomannomutase, a mannose-1-phosphate guanylyltransferase, a GDP mannose-4,6-dehydratase, and a GDP-L-fucose synthase.

Specific examples of the metabolic pathway branching off from a biosynthetic pathway for producing GDP-fucose from a saccharide to a metabolic product other than a target substance include a known metabolic pathway such as a metabolic pathway from GDP-fucose to colanic acid.

2) A microorganism used as a host cell that is artificially endowed or enhanced with an ability to supply a receptor carbohydrate, which is a reaction substrate for a fucosyltransferase Examples of the method for artificially endowing or enhancing an ability to supply a receptor carbohydrate to a microorganism used as a host cell include the following (2a) to (2g). These methods may be used alone or in combination.

(2a) A method of alleviating or releasing at least one mechanism for controlling a biosynthetic pathway for producing a receptor carbohydrate from a saccharide (2b) A method of enhancing expression of at least one enzyme associated with a biosynthetic pathway for producing a receptor carbohydrate from a saccharide (2c) A method of increasing the number of copies of at least one gene encoding an enzyme associated with a biosynthetic pathway for producing a receptor carbohydrate from a saccharide (2d) A method of alleviating or releasing at least one mechanism for decomposing a receptor carbohydrate (2e) A method of enhancing an expression of at least one enzyme associated with intracellular uptake of a receptor carbohydrate (2f) A method of increasing the number of copies of at least one gene encoding an enzyme associated with intracellular uptake of a receptor carbohydrate (2g) A method of weakening or blocking at least one metabolic pathway branching off from a receptor carbohydrate to a metabolic product other than a target substance Specific examples of the enzyme associated with a biosynthetic pathway for producing a receptor carbohydrate from a saccharide include known enzymes such as an enzyme having a lactose synthase activity for producing lactose using glucose and UDP-galactose as substrates. Specific examples of the mechanism for decomposing a receptor carbohydrate include known enzymes such as β-galactosidase that catalyzes hydrolysis of lactose to produce glucose and galactose.

Specific examples of the enzyme associated with intracellular uptake of a receptor carbohydrate include known enzymes such as lactose permease associated with intracellular uptake of lactose. Specific examples of the method for endowing or enhancing an ability to supply a receptor carbohydrate include known methods such as a method of reducing or inactivating an activity of β-galactosidase by a genetic manipulation (Metabolic Engineering, 2017, 41: 23-38).

Examples of the method for introducing the recombinant DNA of the above 3 as an autonomously replicatable plasmid in a host cell include the above-described method using calcium ions, protoplast method, and electroporation method, a spheroplast method (Proc. Natl. Acad. Sci., USA, 81, 4889, 1984), and a lithium acetate method (J. Bacteriol., 153, 163, 1983).

Examples of the method for incorporating a recombinant DNA into a chromosome of a host cell include a homologous recombination method. Examples of the homologous recombination method include a method using a plasmid for homologous recombination that can be prepared by ligating with a plasmid DNA comprising a drug resistance gene that cannot autonomously replicate in a host cell to be introduced. Examples of the method using homologous recombination frequently used in *Escherichia coli* include a method of introducing a recombinant DNA using a homologous recombination system of a lambda phage (Proc.Natl.Acad.Sci. USA, 97, 6641 to 6645, 2000).

Further, by using a selection method based on the fact that *Escherichia coli* becomes sucrose-sensitive due to a *Bacillus subtilis* revansucrase incorporated on a chromosome together with a recombinant DNA, or a selection method based on the fact that *Escherichia coli* becomes streptomycin-sensitive by incorporating a wild-type rpsL gene into

*Escherichia coli* comprising a mutant rpsL gene for streptomycin resistance [Mol. Microbiol., 55, 137 (2005), Biosci. Biotechnol. Biochem., 71, 2905 (2007)], *Escherichia coli* with a target region on a chromosomal DNA of the host cell substituted with the recombinant DNA can be obtained.

The fact that the transformant obtained by the above method contains the DNA of the present invention according to the above 2 can be confirmed by, for example, in the case where the transformant is a transformant obtained by transforming a host cell having an ability to produce GDP-fucose or a receptor carbohydrate from a saccharide, culturing the transformant in a culture medium, and comparing the production amount of fucose-containing carbohydrate accumulated in the culture product with that of a parent strain. It can also be confirmed by preparing an extract containing the protein of the present invention from the culture product, causing the extract, GDP-fucose, and a receptor carbohydrate to exist in an aqueous medium, and comparing the production amount of fucose-containing carbohydrate accumulated in the aqueous medium with that of a parent strain.

5. Method for Producing Fucose-containing Carbohydrate of Present Invention

The method for producing a fucose-containing carbohydrate of the present invention is a method according to the following 5-1 and 5-2.

5-1. Method for Producing Fucose-containing Carbohydrate by Fermentation Method

Examples of the method for producing a fucose-containing carbohydrate of the present invention include a method of producing a fucose-containing carbohydrate by a fermentation method including culturing the transformant of the above 4 in a culture medium to produce a fucose-containing carbohydrate.

The transformant of the present invention used in the method of producing a fucose-containing carbohydrate by a fermentation method is preferably a transformant having an ability to produce GDP-fucose from a saccharide.

As the transformant of the present invention used in the method of producing a fucose-containing carbohydrate by a fermentation method, a transformant having an ability to produce a receptor carbohydrate may be used.

The method of culturing the transformant in the above 4 can be performed according to a method generally used for culturing a microorganism.

As a culture medium for culturing the transformant, any of a natural culture medium and a synthetic culture medium may be used as long as the culture medium contains a carbon source, a nitrogen source, an inorganic salt, and the like that can be assimilated by the transformant and can efficiently culture the transformant.

Any carbon source may be used as long as it can be assimilated by the transformant, and examples thereof include saccharides such as glucose, fructose, sucrose, molasses containing these, starch, or a starch hydrolysate, organic acids such as acetic acid or propionic acid, or alcohols such as glycerol, ethanol, or propanol.

Examples of the nitrogen source include ammonium salts of inorganic acids or organic acids such as ammonia, ammonium chloride, ammonium sulfate, ammonium acetate, or ammonium phosphate, other nitrogen-containing compounds thereof, peptone, a meat extract, a yeast extract, a corn steep liquor, a casein hydrolysate, a soybean meal, a soybean meal hydrolysate, various fermented bacterial cells, and digestive products thereof.

Examples of the inorganic salt include potassium primary phosphate, potassium secondary phosphate, magnesium phosphate, magnesium sulfate, sodium chloride, ferrous sulfate, manganese sulfate, copper sulfate, and calcium carbonate. A receptor carbohydrate such as lactose as a precursor of a fucose-containing carbohydrate may be added to the culture medium, or GTP, mannose, or the like as a precursor of GDP-fucose may be added to the culture medium.

In the method of producing a fucose-containing carbohydrate by a fermentation method, when the transformant to be used does not have the ability to produce GDP-fucose, GDP-fucose is added to the culture medium during culture. In the method of producing a fucose-containing carbohydrate by a fermentation method, when the transformant to be used does not have the ability to produce GDP-fucose, instead of adding GDP-fucose to the culture medium, GDP-fucose may be supplied to the transformant of the present invention by culturing microorganisms having the ability to produce GDP-fucose from a saccharide simultaneously with the transformant of the present invention.

In order to supply or enhance GTP, which is a precursor of GDP-fucose, microorganisms having the ability to produce GTP may be simultaneously cultured. Examples of the microorganism having the ability to produce GTP include known microorganisms such as a microorganism in which expression of an enzyme associated with a biosynthetic pathway of GTP is enhanced by various genetic manipulations (Biotechnol Bioeng, Sep. 3: 2019, 2412 to 2417).

In the method of producing a fucose-containing carbohydrate by a fermentation method, when the transformant to be used does not have the ability to produce a receptor carbohydrate such as lactose, a receptor carbohydrate such as lactose is added to the culture medium during culture.

In the method of producing a fucose-containing carbohydrate by a fermentation method, when the transformant to be used does not have the ability to produce a receptor carbohydrate such as lactose, instead of adding a receptor carbohydrate such as lactose to the culture medium during culture, a receptor carbohydrate such as lactose may be supplied to the transformant of the present invention by culturing microorganisms having the ability to produce a receptor carbohydrate such as lactose from a saccharide simultaneously with the transformant of the present invention.

The culture is generally preferably performed under preferred conditions such as shaking culture or deep aeration stirring culture. The culture temperature is generally 15° C. to 40° C., and the culture time is generally 5 hours to 7 days. The pH of the culture solution during culture is generally maintained at 3.0 to 9.0. The pH is adjusted using an inorganic or organic acid, an alkaline solution, urea, calcium carbonate, ammonia, or the like.

If necessary, antibiotics such as ampicillin and tetracycline may be added to the culture medium during the culture. When culturing a microorganism transformed with an expression vector using an inducible promoter as a promoter, an inducer may be added to the culture medium as necessary. For example, isopropyl-$\beta$-D-thiogalactopyranoside (IPTG) or the like may be added to the culture medium when culturing a microorganism transformed with an expression vector using a lac promoter, and indole acrylic acid or the like may be added to the culture medium when culturing a microorganism transformed with an expression vector using a trp promoter.

By producing a fucose-containing carbohydrate in the culture product by the above-described culture to produce the fucose-containing carbohydrate, the fucose-containing carbohydrate can be obtained by, for example, collecting the fucose-containing carbohydrate accumulated in the transformant or the culture product.

The obtained fucose-containing carbohydrate can be analyzed by a general method using carbohydrate ion chromatography or the like. The collection of the fucose-containing carbohydrate from the culture product or the processed product of the culture product can be performed by a general method using activated carbon, an ion exchange resin, or the like. When the fucose-containing carbohydrate is accumulated in bacterial cells, for example, the fucose-containing carbohydrate can be collected, by using activated carbon, an ion exchange resin, or the like, from a supernatant obtained by homogenizing the bacterial cells by ultrasonic waves or the like and removing the bacterial cells by centrifugation.

5-2. Method for Producing Fucose-containing Carbohydrate using GDP-fucose and Receptor Carbohydrate as Substrates Examples of the method for producing a fucose-containing carbohydrate of the present invention include a method for producing a fucose-containing carbohydrate using GDP-fucose and a receptor carbohydrate as precursors. Specifically, a culture product obtained by culturing the transformant of the above 4 or a processed product of the culture product can be used as an enzyme source, and the enzyme source, GDP-fucose, and a receptor carbohydrate can be caused to exist in an aqueous medium to generate a fucose-containing carbohydrate in an aqueous medium, and the fucose-containing carbohydrate produced in the aqueous medium can be collected as necessary.

The GDP-fucose and the receptor carbohydrate are not limited as long as they can serve as a substrate of the protein of the present invention possessed by the transformant of the present invention, and a culture product of a microorganism having an ability to produce GDP-fucose or a receptor carbohydrate, or a processed product of the culture product may be used as it is, or the GDP-fucose and the receptor carbohydrate collected from the culture product or the processed product of the culture product may be used.

Examples of the processed product of the culture product include a concentrate of the culture product, a dried product of the culture product, a bacterial cell obtained by centrifuging the culture product, a dried product of the bacterial cell, a freeze-dried product of the bacterial cell, a surfactant processed product of the bacterial cell, an ultrasonic processed product of the bacterial cell, a mechanical trituration processed product of the bacterial cell, a solvent processed product of the bacterial cell, an enzyme processed product of the bacterial cell, a protein fraction of the bacterial cell, an immobilized product of the bacterial cell, and an enzyme preparation obtained by extraction from the bacterial cell.

Examples of the aqueous medium include water, buffers such as phosphate, carbonate, acetate, borate, citrate and Tris, alcohols such as methanol and ethanol, esters such as ethyl acetate, ketones such as acetone, and amides such as acetamide. A microorganism culture solution used as an enzyme source may be used as the aqueous medium.

The method for analyzing and collecting the fucose-containing carbohydrate produced in the aqueous medium is the same as that of 5-1.

Analysis Example

In Examples, analysis and quantification of 3-fucosyllactose were performed by the following procedure. A culture solution containing microorganisms after culture was centrifuged, and the supernatant was collected. 3-Fucosyllactose contained in the supernatant was analyzed by a carbohydrate analyzer ICS-5000 (manufactured by Thermo Fisher Scientific K.K.)

[Analysis Conditions]
Column: CarboPAC PA1
Column temperature: 25° C.
Mobile phase: (mobile phase A) water
(mobile phase B) 500 mmol/L sodium hydroxide
(mobile phase C) 300 mmol/L sodium acetate
Mobile phase A, mobile phase B, and mobile phase C mixing ratio:
(0 minutes to 10 minutes) 80:20:0
(10 minutes to 15 minutes) gradient from 80:20:0 to 70:20:10
(15 minutes to 17 minutes) gradient from 70:20:10 to 0:20:80
(17 minutes to 25 minutes) 0:20:80
(25 minutes to 35 minutes) 80:20:0
Flow rate: 1.0 mL/min
Detector: pulsed amperometric detector Example Examples of the invention are shown below, but the invention is not limited to these Examples.

[Example 1] Construction of Microorganism Used for Production of 3-Fucosyllactose (1) Acquisition of DNA Fragment to be Used as Marker for Gene Deletion PCR was performed using, as a primer set, DNAs consisting of the nucleotide sequences shown in "Primer set" in Table 1 and using, as a template, a DNA described in "Template" in Table 1 to obtain each amplified DNA fragment. PGP-21rT

TABLE 1

| Primer set (SEQ ID NO:) | Template | Amplified DNA fragment |
|---|---|---|
| 8 and 9 | pHSG396 (manufactured by Takara Bio Inc.) | cat |
| 10 and 11 | Genomic DNA of *Bacillus subtilis* 168 strain | sacB |

A genomic DNA of a *Bacillus subtilis* 168 strain was prepared by a standard method. The cat of the amplified DNA fragment contains about 200 bp upstream to about 50 bp downstream of the cat gene on pHSG396. The sacB of the amplified DNA fragment contains about 300 bp upstream to about 100 bp downstream of the sacB gene on the genomic DNA of the *Bacillus subtilis* 168 strain.

Next, PCR was performed using, as a template, the cat and sacB of the amplified DNA fragment and using, as a primer set, DNAs consisting of the nucleotide sequences represented by SEQ ID NOs: 8 and 11 to obtain a DNA fragment comprising the cat gene and the sacB gene (hereinafter, referred to as cat-sacB).

(2) Construction of *Escherichia coli* with Loss of β-Galactosidase Activity, Lactose Permease Activity, and Colanic Acid Producing Activity

*Escherichia coli* deficient in DNA encoding β-galactosidase (hereinafter, referred to as lacZ gene), DNA encoding lactose permease (hereinafter, referred to as lacY gene), and DNA encoding a colanic acid production-related protein (hereinafter, referred to as wcaJ, wzxC, wcaK, wcaL, or wcaM gene) was constructed by the following method. Note that the lacZ and lacY (hereinafter, referred to as lacZY), and wcaJ, wzxC, wcaK, wcaL, and weaM (hereinafter, referred to as wcaJ-wzxC-wcaKLM) each form an operon on the *Escherichia coli* genome.

PCR was performed using, as a template, a genomic DNA of the *Escherichia coli* W3110 strain prepared by an ordinary method and using, as a primer set, DNAs consisting of the nucleotide sequences shown in "Primer set" in Table 2 to amplify each DNA fragment.

TABLE 2

| Primer set (SEQ ID NO:) | Amplified DNA fragment | Remark |
|---|---|---|
| 12 and 13 | lacZ upstream 1 | Sequences at 5' ends of nucleotide sequences represented by SEQ ID NOs: 8 and 12 are complementary |
| 14 and 15 | lacY downstream 1 | Sequences at 5' ends of nucleotide sequences represented by SEQ ID NOs: 11 and 14 are complementary |
| 13 and 16 | lacZ upstream 2 | Sequences at 5' ends of nucleotide sequences represented by SEQ ID NOs: 16 and 17 are complementary |
| 15 and 17 | lacY downstream 2 | |

The lacZ upstream 1 and lacZ upstream 2 include a region from an initiation codon of the lacZ gene to about 1000 bp upstream of the initiation codon. The lacY downstream 1 and a lacY downstream 2 include a region from about 50 bp to about 1000 bp downstream of a stop codon of the lacY gene.

PCR was performed using, as a template, a mixture of the lacZ upstream 1, the lacY downstream 1, and the cat-sacB fragment at an equimolar ratio and using, as a primer set, DNAs consisting of the nucleotide sequences represented by SEQ ID NOs: 13 and 15 to obtain a DNA fragment consisting of a sequence with the cat-sacB fragment inserted in a region around the lacZ and lacY genes (hereinafter, referred to as lacZY::cat-sacB).

PCR was performed using, as a template, a mixture of the lacZ upstream 2 and the lacY downstream 2 at an equimolar ratio and using, as a primer set, DNAs consisting of the nucleotide sequences represented by SEQ ID NOs: 13 and 15 to obtain a DNA fragment consisting of a sequence with the lacZ upstream and the lacY downstream directly linked to each other without lacZY (hereinafter, referred to as ΔlacZY).

The lacZY::cat-sacB fragment was introduced into a W3110 strain carrying a plasmid pKD46 comprising a gene encoding, recombinase (Datsenko, K. A., Warner, B. L. L., Proc. Natl. Acad.Sci, USA, Vol. 97, 6640-6645, 2000) by an electroporation method to obtain a transformant (a transformant with the lacZY gene substituted with lacZY::cat-sacB) exhibiting chloramphenicol resistance and sucrose sensitivity.

The ΔlacZY fragment was introduced into the transformant by the electroporation method to obtain a transformant (a transformant with lacZY::cat-sacB substituted with ΔlacZY) exhibiting chloramphenicol sensitivity and sucrose resistance. Among them, a transformant (a transformant without pKD46) exhibiting ampicillin sensitivity was further obtained. The transformant was named W3110ΔlacZY.

Similarly, PCR was performed using, as a template, the genomic DNA of the W3110 strain and using, as a primer set, DNAs consisting of the nucleotide sequence shown in "Primer set" in Table 3 to obtain each amplified DNA fragment.

TABLE 3

| Primer set (SEQ ID NO:) | Amplified DNA fragment | Remark |
|---|---|---|
| 18 and 19 | wcaJ upstream 1 | Sequences at 5' ends of nucleotide sequences represented by SEQ ID NOs: 8 and 18 are complementary |
| 20 and 21 | wcaM downstream 1 | Sequences at 5' ends of nucleotide sequences represented by SEQ ID NOs: 11 and 20 are complementary |
| 19 and 22 | wcaJ upstream 2 | Sequences at 5' ends of nucleotide sequences represented by SEQ ID NOs: 22 and 23 are complementary |
| 21 and 23 | wcaM downstream 2 | |

The wcaJ upstream 1 and the wcaJ upstream 2 include a region from an initiation codon of the wcaJ gene to about 1000 bp upstream of the initiation codon. The wcaM downstream 1 and the wcaM downstream 2 include a region from a stop codon of the weaM gene to about 1000 bp downstream of the stop codon.

PCR was performed using, as a template, a mixture of the wcaJ upstream 1, the wcaM downstream 1, and the cat-sacB fragment at an equimolar ratio and using, as a primer set, DNAs consisting of the nucleotide sequences represented by SEQ ID NOs. 19 and 21 to obtain a DNA fragment consisting of a sequence with the cat-sacB fragment inserted in a region around a wcaJ-wzxC-wcaKLM operon (hereinafter, referred to as wcaJ-wzxC-wcaKLM::cat-sacB).

PCR was performed using, as a template, a mixture of the wcaJ upstream 2 and the wcaM downstream 2 at an equimolar ratio and using, as a primer set, DNAs consisting of the nucleotide sequences represented by SEQ ID NOs: 19 and 21 to obtain a DNA fragment consisting of a sequence with the wcaJ upstream and the wcaM downstream directly linked to each other without wcaJ-wzxC-wcaKLM (hereinafter, referred to as ΔwcaJ-wzxC-wcaKLM).

The wcaJ-wzxC-wcaKLM::cat-sacB fragment was introduced into the W3110 ΔlacZY strain constructed as described above by the electroporation method to obtain a transformant (a transformant with wcaJ-wzxC-wcaKLM substituted with wcaJ-wzxC-wcaKLM::cat-sacB) exhibiting chloramphenicol resistant and sucrose sensitivity.

The ΔwcaJ-wzxC-wcaKLM fragment was introduced into the transformant by the electroporation method to obtain a transformant (a transformant with wcaJ-wzxC-wcaKLM:: cat-sacB substituted with ΔwcaJ-wzxC-wcaKLM) exhibiting chloramphenicol sensitivity and sucrose resistance. Further, a transformant (a transformant without pKD46) exhibiting ampicillin sensitivity was obtained. The transformant was named T166.

(3) Construction of Microorganism Having α1,3-Fucosyltransferase Activity (Hereinafter, Referred to as 1,3-FucT Activity)

*Escherichia coli* comprising a gene expression plasmid encoding a *Bacteroides* reticulotermitis-derived glycosyltransferase consisting of the amino acid sequence represented by SEQ ID NO: 2 (hereinafter referred to as BrFucT) was constructed by the following method.

PCR was performed using, as a primer set, DNAs consisting of the nucleotide sequences shown in "Primer set" in Table 4 and using, as a template, a DNA described in "Template" in Table 4 to obtain each amplified DNA fragment.

TABLE 4

| Primer set (SEQ ID NO:) | Template | Amplified DNA fragment |
|---|---|---|
| 24 and 25 | Genomic DNA of *Escherichia coli* W3110 strain | rcsA |
| 28 and 29 | Genomic DNA of Bacteroides reticulotermitis JCM10512 strain | BrFucT |
| 34 and 35 | Genomic DNA of *Escherichia coli* W3110 strain | lacY |

Genomic DNAs of the *Escherichia coli* W3110 strain and the *Bacteroides* reticulotermitis JCM 10512 strain were prepared by an ordinary method. The nucleotide sequences represented by SEQ ID NOs: 25 and 28 and SEQ ID NOs: 29 and 34 comprise complementary sequences at each 5' end.

PCR was performed using, as a template, a mixture of the rcsA, BrFucT, and lacY fragments at an equimolar ratio and using, as a primer set, DNAs consisting of the nucleotide sequences represented by SEQ ID NOs: 36 and 37 to obtain a DNA fragment with the three fragments linked (hereinafter, referred to as rcsA-BrFucT-lacY).

PCR was performed using, as a primer set, DNAs consisting of the nucleotide sequences represented by SEQ ID NOs: 38 and 39 and using, as a template, a plasmid pPE167 (Appl. Environ. Microbiol. 2007, 73: 6378-6385) to obtain a vector fragment of about 4.4 kb.

In this case, the nucleotide sequences represented by SEQ ID NOs: 36 and 39 and SEQ ID NOs: 37 and 38 comprise complementary sequences at each 5' end.

The rcsA-BrFucT-lacY fragment and the vector fragment obtained above were ligated using an In-Fusion HD Cloning Kit (manufactured by Takara Bio Inc.) to obtain a BrFucT-expressing plasmid pATY2.

The T166 strain constructed in Example 1(2) was transformed using the expression plasmid pATY2 to construct *Escherichia coli* having BrFucT, which was named T166/pATY2 strain.

(4) Construction of Microorganism Expressing Modified BrFucT

*Escherichia coli* comprising a gene expression plasmid encoding a modified BrFucT consisting of the amino acid sequence represented by SEQ ID NO: 4 was constructed by the following method.

PCR was performed using, as a primer set, DNAs consisting of the nucleotide sequences shown in "Primer set" in Table 5 and using, as a template, a DNA described in "Template" in Table 5 to obtain each amplified DNA fragment.

TABLE 5

| Primer set (SEQ ID NO:) | Template | Amplified DNA fragment |
|---|---|---|
| 24 and 25 | Genomic DNA of *Escherichia coli* W3110 strain | rcsA |
| 28 and 30 | Genomic DNA of Bacteroides reticulotermitis JCM10512 strain | cBrFucT upstream |
| 31 and 32 | DNA consisting of nucleotide sequence represented by SEQ ID NO: 7 | cBrFucT midstream |
| 29 and 33 | Genomic DNA of Bacteroides reticulotermitis JCM10512 strain | cBrFucT downstream |
| 34 and 35 | Genomic DNA of *Escherichia coli* W3110 strain | lacY |

Genomic DNAs of the *Escherichia coli* W3110 strain and the *Bacteroides* reticulotermitis JCM 10512 strain were prepared by an ordinary method. A DNA consisting of the nucleotide sequence represented by SEQ ID NO: 7 is a DNA obtained by codon-optimizing, for expression in *Escherichia coli*, a partial sequence of a gene encoding *Bacteroides fragilis*-derived α1,3-fucosyltransferase (hereinafter, referred to as BfFucT). The nucleotide sequences represented by SEQ ID NOs: 25 and 28, SEQ ID NOs: 30 and 31, SEQ ID NOs: 32 and 33, and SEQ ID NOs: 29 and 34 comprise complementary sequences at each 5' end.

First, PCR was performed using, as a template, a mixture of three fragments of the cBrFucT upstream, the cBrFucT midstream, and the cBrFucT downstream at an equimolar ratio and using, as a primer set, DNAs consisting of the nucleotide sequences represented by SEQ ID NOs: 28 and 29 to obtain a DNA fragment with the three fragments linked (hereinafter, referred to as cBrFucT fragment).

PCR was performed using, as a template, a mixture of the rcsA and cBrFucT gene, and the lacY fragment at an equimolar ratio and using, as a primer set, DNAs consisting of the nucleotide sequences represented by SEQ ID NOs: 36 and 37 to obtain a DNA fragment with the three fragments linked (hereinafter, referred to as rcsA-cBrFucT-lacY).

PCR was performed using, as a primer set, DNAs consisting of the nucleotide sequences represented by SEQ ID NOs: 38 and 39 and using, as a template, a plasmid pPE167 (Appl. Environ. Microbiol. 2007, 73: 6378-6385) to obtain a vector fragment of about 4.4 kb.

In this case, the nucleotide sequences represented by SEQ ID NOs: 36 and 39 and SEQ ID NOs: 37 and 38 comprise complementary sequences at each 5' end.

The rcsA-cBrFucT-lacY fragment and the vector fragment obtained above were ligated using an In-Fusion HD Cloning Kit (manufactured by Takara Bio Inc.) to obtain a cBrFucT-expressing plasmid pATY3.

The T166 strain constructed in Example 1(2) was transformed using the above expression plasmid pATY3 to construct *Escherichia coli* having cBrFucT, which was named T166/pATY3 strain.

[Comparative Example] Construction of Microorganism with Enhanced Expression of *Bacteroides fragilis*-Derived α1,3-Fucosyltransferase (Hereinafter, Referred to as BfFucT)

PCR was performed using, as a primer set, DNAs consisting of the nucleotide sequences shown in "Primer set" in Table 6 and using, as a template, a DNA described in "Template" in Table 6 to obtain each amplified DNA fragment.

TABLE 6

| Primer set (SEQ ID NO:) | Template | Amplified DNA fragment |
|---|---|---|
| 24 and 25 | Genomic DNA of *Escherichia coli* W3110 strain | rcsA |
| 26 and 27 | Genomic DNA of Bacteroides fragilis ATCC25285 strain | BfFucT |
| 34 and 35 | Genomic DNA of *Escherichia coli* W3110 strain | lacY |

Genomic DNAs of the *Escherichia coli* W3110 strain and the *Bacteroides fragilis* ATCC25285 strain were prepared by an ordinary method. The nucleotide sequences represented by SEQ ID NOs: 25 and 26 and SEQ ID NOs: 27 and 34 comprise complementary sequences at each 5' end.

PCR was performed using, as a template, a mixture of the rcsA and BfFucT gene, and the lacY fragment at an equimolar ratio and using, as a primer set, DNAs consisting of the nucleotide sequences represented by SEQ ID NOs: 36 and 37 to obtain a DNA fragment with the three fragments linked (hereinafter, referred to as rcsA-BfFucT-lacY).

PCR was performed using, as a primer set, DNAs consisting of the nucleotide sequences represented by SEQ ID NOs: 38 and 39 and using, as a template, a plasmid pPE167 (Appl. Environ. Microbiol. 2007, 73: 6378-6385) to obtain a vector fragment of about 4.4 kb. In this case, the nucleotide sequences represented by SEQ ID NOs: 36 and 39 and SEQ ID NOs: 37 and 38 comprise complementary sequences at each 5' end.

The rcsA-BfFucT-lacY fragment and the vector fragment obtained above were ligated using an In-Fusion HD Cloning Kit (manufactured by Takara Bio Inc.) to obtain a BfFucT-expressing plasmid pATY1.

The T166 strain constructed in Example 1(2) was transformed using the above expression plasmid pATY1 to construct *Escherichia coli* having BfFucT, which was named T166/pATY1 strain.

[Example 2] Production of 3-Fucosyllactose

The T166/pATY1 strain, the T166/pATY2 strain, and the T166/pATY3 strain obtained in Example 1 were incubated on LB plates at 30° C. for 24 hours, inoculated into large-sized test tubes each containing 4 mL of an LB culture medium containing 100 mg/L of kanamycin, and shaking-cultured at 30° C. for 18 hours. Thereafter, 0.2 mL of each obtained culture solution was inoculated into a large-sized test tube containing 4 mL of a production culture medium [glucose 30 g/L, lactose monohydrate 10 g/L, magnesium sulfate heptahydrate 2 g/L, dipotassium hydrogen phosphate 16 g/L, potassium dihydrogen phosphate 14 g/L, ammonium sulfate 2 g/L, citric acid 1 g/L, casamino acid 5 g/L, thiamine hydrochloride 10 mg/L, ferrous sulfate heptahydrate 50 mg/L, manganese sulfate pentahydrate 10 mg/L (adjusted to pH 7.2 by aqueous sodium hydroxide, except for glucose, lactose monohydrate, and magnesium sulfate heptahydrate, and then autoclaved) (aqueous solutions containing glucose, lactose monohydrate, and magnesium sulfate heptahydrate were separately prepared, autoclaved, cooled, and then mixed)] containing 100 mg/L of kanamycin, and shaking-cultured at 30° C. for 28 hours.

After completion of the culture, the culture solution was appropriately diluted and centrifuged, and 3-fucosyllactose contained in the supernatant was analyzed by a carbohydrate analyzer ICS-5000. The results are shown in Table 7.

TABLE 7

| Strain name | Expression | 3-fucosyllactose (mg/L) |
|---|---|---|
| T166/pATY1 | BfFucT | 399 |
| T166/pATY2 | BrFucT | 1033 |
| T166/pATY3 | cBrFucT | 1223 |

As shown in Table 7, it was found that compared to the T166/pATY1 strain, the T166/pATY2 strain and the T166/pATY3 strain exhibited remarkably high 3-fucosyllactose productivity, and BrFucT and cBrFucT both had a 1,3-FucT activity.

It is also found that the use of BrFucT and cBrFucT significantly improves the 3-fucosyllactose productivity as compared with BfFucT, which is a known α1,3-FucT.

Although the present invention has been described in detail with reference to specific embodiments, it will be apparent to those skilled in the art that various changes and modifications can be made without departing from the spirit and scope of the invention. The present application is based on a Japanese Patent Application No. 2021-018483 filed on Feb. 8, 2021, the entire contents of which are incorporated herein by reference. All references cited herein are incorporated in their entirety.

Sequence Listing Free Text

SEQ ID NO: 1: nucleotide sequence of brfucT derived from *Bacteroides* reticulotermitis SEQ ID NO: 2: amino acid sequence of BrfucT derived from *Bacteroides* reticulotermitis SEQ ID NO: 3: nucleotide sequence of cbrfucT derived from *Bacteroides* reticuloterimis and *B. fragilis*

SEQ ID NO: 4: amino acid sequence of cBrfucT derived from *Bacteroides* reticuloterimis and *B. fragilis*

SEQ ID NO: 5: nucleotide sequence of bffucT derived from *Bacteroides fragilis*

SEQ ID NO: 6: amino acid sequence of BffucT derived from *Bacteroides fragilis*

SEQ ID NO: 7: partial nucleotide sequence of codon optimized BfFucT

SEQ ID NOs: 8 and 9: nucleotide sequences of cat amplification primers

SEQ ID NOs: 10 and 11: nucleotide sequences of sacB amplification primers

SEQ ID NOs: 12 and 13: nucleotide sequences of lacZ upstream 1 amplification primers SEQ ID NOs: 14 and 15: nucleotide sequences of lacY downstream 1 amplification primers SEQ ID NO: 16: nucleotide sequence of lacZ upstream 2 amplification primer SEQ ID NO: 17: nucleotide sequence of lacY downstream 2 amplification primer SEQ ID NOs: 18 and 19: nucleotide sequences of wcaJ upstream 1 amplification primers SEQ ID NOs: 20 and 21: nucleotide sequences of wcaM downstream 1 amplification primers SEQ ID NO: 22: nucleotide sequence of wcaJ upstream 2 amplification primer SEQ ID NO: 23: nucleotide sequence of wcaM downstream 2 amplification primer SEQ ID NOs: 24 and 25: nucleotide sequences of rcsA amplification primers SEQ ID NOs: 26 and 27: nucleotide sequences of bffucT amplification primers SEQ ID NOs: 28 and 29: nucleotide sequences of brfucT amplification primers SEQ ID NO: 30: nucleotide sequence of cBrFucT upstream amplification primer SEQ ID NOs: 31 and 32: nucleotide sequences of cBrFucT midstream amplification primers SEQ ID NO: 33: nucleotide sequence of cBrFucT downstream amplification primer SEQ ID NOs: 34 and 35: nucleotide sequences of lacY amplification primers SEQ ID NOs: 36 and 37: nucleotide sequences of rcsA-cBrFucT-lacY amplification primers SEQ ID NOs: 38 and 39: nucleotide sequences of pPE167 amplification primers

The invention claimed is:

1. A protein having an α1,3-fucosyltransferase activity, the protein comprising the amino acid sequence set forth in SEQ ID NO: 4.

2. An isolated DNA encoding the protein of claim 1, the DNA comprising the polynucleotide sequence set forth in SEQ ID NO: 3.

3. A recombinant DNA comprising the DNA according to claim 2.

4. An isolated host cell obtained by transforming the host cell with the recombinant DNA according to claim 3.

5. The host cell according to claim 4, wherein the host cell is *Escherichia coli.*

6. A method for producing a fucose-containing carbohydrate, comprising: culturing the host cell according to claim 4 in a culture medium to produce a fucose-containing carbohydrate.

7. The method according to claim 6, wherein the fucose-containing carbohydrate is 3-fucosyllactose.

* * * * *

SEQUENCE LISTING

<160> NUMBER OF SEQ ID NOS: 39

<210> SEQ ID NO 1
<211> LENGTH: 951
<212> TYPE: DNA
<213> ORGANISM: Bacteroides reticulotermitis

<400> SEQUENCE: 1

```
atgaaattga aagtgaaatt tgtagatttt tgggatggct ttgatgaaca ttataatact      60
ttcgttaatg ttctatctga gaaatatgaa atcgaaattt gtgatcatcc tgattactta     120
atatattcga cttttggata taagaactta aagtacgaaa attgtgttaa gatattttat     180
acgggtgaaa atataactcc agactttaat ctttgtgatt atgcgattgg ctttgatata     240
atggaattcg gagatcgcta tatgcgccta ccattatatg ccttatatgg tattgaagag     300
ttgcgtaaac ctaaagtctt taattcacag gaagctctga atcggaaatt ctgtagtttt     360
gttgtctcta atggagctga tgctcctgaa aggacccgtt tctttcattt actttcagaa     420
tataagcagg tagattcagg aggagcatat gagaataatg ttggtgggcg agttgttgat     480
aagaaatttt ttatttctaa ctataaattc aatattgctt ttgaaaatag tgctaaagac     540
ggatatacta cagagaaaat tatggagccg atgttggtaa actctctgcc gatatattgg     600
ggaaacagat tggttgagtt ggattttaat cctaattctt ttattaatgc tgcagattac     660
ccatctttag aagctttggt agaatatatc gttgagttgg acacaaatga tgataaatat     720
ctgtcaattt tgtcaagacc ttggcttaac aaaagtaatt atttggattg gcaagaaagg     780 cttttttagct tctttgagaa tgttttcaat aaaccattga atgaacagaa atatttatca     840 cctttatgggt acggtaagct atatagaaga agattaatgg aaatgtatat tgcgaaaaga     900
aaattgaaaa aatggaaaat ggtttgtaac ccttgtcgtt ggtttagatg a             951
```

<210> SEQ ID NO 2
<211> LENGTH: 316
<212> TYPE: PRT
<213> ORGANISM: Bacteroides reticulotermitis

<400> SEQUENCE: 2

```
Met Lys Leu Lys Val Lys Phe Val Asp Phe Trp Asp Gly Phe Asp Glu
1               5                   10                  15

His Tyr Asn Thr Phe Val Asn Val Leu Ser Glu Lys Tyr Glu Ile Glu
            20                  25                  30

Ile Cys Asp His Pro Asp Tyr Leu Ile Tyr Ser Thr Phe Gly Tyr Lys
        35                  40                  45

Asn Leu Lys Tyr Glu Asn Cys Val Lys Ile Phe Tyr Thr Gly Glu Asn
    50                  55                  60

Ile Thr Pro Asp Phe Asn Leu Cys Asp Tyr Ala Ile Gly Phe Asp Ile
65                  70                  75                  80

Met Glu Phe Gly Asp Arg Tyr Met Arg Leu Pro Leu Tyr Ala Leu Tyr
                85                  90                  95

Gly Ile Glu Glu Leu Arg Lys Pro Lys Val Phe Asn Ser Gln Glu Ala
            100                 105                 110

Leu Asn Arg Lys Phe Cys Ser Phe Val Val Ser Asn Gly Ala Asp Ala
        115                 120                 125

Pro Glu Arg Thr Arg Phe Phe His Leu Leu Ser Glu Tyr Lys Gln Val
    130                 135                 140

Asp Ser Gly Gly Ala Tyr Glu Asn Asn Val Gly Gly Arg Val Val Asp
145                 150                 155                 160
```

```
Lys Lys Phe Phe Ile Ser Asn Tyr Lys Phe Asn Ile Ala Phe Glu Asn
                165                 170                 175

Ser Ala Lys Asp Gly Tyr Thr Thr Glu Lys Ile Met Glu Pro Met Leu
                180                 185                 190

Val Asn Ser Leu Pro Ile Tyr Trp Gly Asn Arg Leu Val Glu Leu Asp
                195                 200                 205

Phe Asn Pro Asn Ser Phe Ile Asn Ala Ala Asp Tyr Pro Ser Leu Glu
            210                 215                 220

Ala Leu Val Glu Tyr Ile Val Glu Leu Asp Thr Asn Asp Asp Lys Tyr
225                 230                 235                 240

Leu Ser Ile Leu Ser Arg Pro Trp Leu Asn Lys Ser Asn Tyr Leu Asp
                245                 250                 255

Trp Gln Glu Arg Leu Phe Ser Phe Phe Glu Asn Val Phe Asn Lys Pro
                260                 265                 270

Leu Asn Glu Gln Lys Tyr Leu Ser Pro Tyr Gly Tyr Gly Lys Leu Tyr
            275                 280                 285

Arg Arg Arg Leu Met Glu Met Tyr Ile Ala Lys Arg Lys Leu Lys Lys
        290                 295                 300

Trp Lys Met Val Cys Asn Pro Cys Arg Trp Phe Arg
305                 310                 315

<210> SEQ ID NO 3
<211> LENGTH: 954
<212> TYPE: DNA
<213> ORGANISM: Bacteroides reticuloterimis and Bacteroides fragilis

<400> SEQUENCE: 3
atgaaattga aagtgaaatt tgtagatttt tgggatggct ttgatgaaca ttataatact      60
ttcgttaatg ttctatctga aaatatgaa atcgaaattt gtgatcatcc tgattactta     120
atatattcga cttttggata taagaactta aagtacgaaa attgtgttaa gatattttat     180
acgggtgaaa atataactcc agactttaat cttttgtgatt atgcgattgg ctttgatata     240
atggaattcg gagatcgcta tatgcgccta ccattatatg ccttatatgg tattgaagag     300
ttgcgtaaac ctaaagtctt taattcacag gaagctctga tcgtaagtt ctgcagcatc     360 gtggttagca ataataaatg ggcggacccg attcgtgaga cctttttcaa actgctgagc     420
agctacaaaa aggtggacag cggtggccgt gcgtggaaca catcggtgg cccggttgac     480 aacaagctgg atttcatcag ccagtacaaa ttcaacattg cgtttgagaa cagccgtgtg     540
ctgggttaca ccaccgaaaa gattatggag ccgatgcaag tgaacagcat tccggtttac     600
tggggtaaca gattggttga gttggatttt aatcctaatt cttttattaa tgctgcagat     660
tacccatctt tagaagcttt ggtagaatat atcgttgagt tggacacaaa tgatgataaa     720
tatctgtcaa ttttgtcaag accttggctt aacaaaagta attatttgga ttggcaagaa     780
aggcttttta gcttctttga gaatgttttc aataaaccat tgaatgaaca gaaatattta     840
tcaccttatg ggtacggtaa gctatataga agaagattaa tggaaatgta tattgcgaaa     900
agaaaattga aaaatggaa aatggtttgt aaccccttgtc gttggtttag atga     954

<210> SEQ ID NO 4
<211> LENGTH: 317
<212> TYPE: PRT
<213> ORGANISM: Bacteroides reticuloterimis and Bacteroides fragilis

<400> SEQUENCE: 4
```

```
Met Lys Leu Lys Val Lys Phe Val Asp Phe Trp Asp Gly Phe Asp Glu
1               5                   10                  15

His Tyr Asn Thr Phe Val Asn Val Leu Ser Glu Lys Tyr Glu Ile Glu
            20                  25                  30

Ile Cys Asp His Pro Asp Tyr Leu Ile Tyr Ser Thr Phe Gly Tyr Lys
        35                  40                  45

Asn Leu Lys Tyr Glu Asn Cys Val Lys Ile Phe Tyr Thr Gly Glu Asn
    50                  55                  60

Ile Thr Pro Asp Phe Asn Leu Cys Asp Tyr Ala Ile Gly Phe Asp Ile
65                  70                  75                  80

Met Glu Phe Gly Asp Arg Tyr Met Arg Leu Pro Leu Tyr Ala Leu Tyr
                85                  90                  95

Gly Ile Glu Glu Leu Arg Lys Pro Lys Val Phe Asn Ser Gln Glu Ala
            100                 105                 110

Leu Asn Arg Lys Phe Cys Ser Ile Val Val Ser Asn Asn Lys Trp Ala
        115                 120                 125

Asp Pro Ile Arg Glu Thr Phe Phe Lys Leu Leu Ser Ser Tyr Lys Lys
        130                 135                 140

Val Asp Ser Gly Gly Arg Ala Trp Asn Asn Ile Gly Gly Pro Val Asp
145                 150                 155                 160

Asn Lys Leu Asp Phe Ile Ser Gln Tyr Lys Phe Asn Ile Ala Phe Glu
                165                 170                 175

Asn Ser Arg Val Leu Gly Tyr Thr Thr Glu Lys Ile Met Glu Pro Met
            180                 185                 190

Gln Val Asn Ser Ile Pro Val Tyr Trp Gly Asn Arg Leu Val Glu Leu
            195                 200                 205

Asp Phe Asn Pro Asn Ser Phe Ile Asn Ala Ala Asp Tyr Pro Ser Leu
        210                 215                 220

Glu Ala Leu Val Glu Tyr Ile Val Glu Leu Asp Thr Asn Asp Asp Lys
225                 230                 235                 240

Tyr Leu Ser Ile Leu Ser Arg Pro Trp Leu Asn Lys Ser Asn Tyr Leu
                245                 250                 255

Asp Trp Gln Glu Arg Leu Phe Ser Phe Phe Glu Asn Val Phe Asn Lys
            260                 265                 270

Pro Leu Asn Glu Gln Lys Tyr Leu Ser Pro Tyr Gly Tyr Gly Lys Leu
        275                 280                 285

Tyr Arg Arg Arg Leu Met Glu Met Tyr Ile Ala Lys Arg Lys Leu Lys
        290                 295                 300

Lys Trp Lys Met Val Cys Asn Pro Cys Arg Trp Phe Arg
305                 310                 315
```

```
<210> SEQ ID NO 5
<211> LENGTH: 996
<212> TYPE: DNA
<213> ORGANISM: Bacteroides fragilis

<400> SEQUENCE: 5
atgtgtgatt gcttgtctat catattgtta gtcaaaatga aaaagattta tttgaaattt       60 gttgatttt gggatggatt tgatactatt tctaacttta ttgtggatgc tttgtccatt      120
caatacgaag tagtactatc taatgagcca gattatttat tctattcatg ttttggaacg      180
tcacatttag aatatgattg tataaaaatc atgtttatag gtgaaaatat agttcctgat      240
tttaacgttt gtgattatgc cataggtttt aattatattg attttgggga ccgttacttg      300
aggttgcctt tatatgctat atatgatgga ttttcaaact tgcagaataa aaagattgat      360
```

-continued

```
gtaaataaag ctttagaccg taaattttgt agtattgttg tttcaaataa taaatgggca      420
gatcctattc gtgagacttt ctttaaatta ctatctagtt ataagaaagt agactctggt      480
ggaagagctt ggaataatat aggaggacct gttgataata aattggattt tattagccaa      540
tataagttta atattgcttt tgaaaatagt agggtactgg gatatacaac agaaaaaata      600
atggaaccta tgcaggtgaa ttctattcca gtatattggg gaaatccttt ggttggtaaa      660
gattttaatg tggactcctt tgtaaatgct catgattttg attctttaga aagattagtt      720
gagtatatta tagaattgga ttcttcaaag gataaatatc tggaaatgtt ggaaaaacct      780
tggcttctcg ataagacata tttggattgg aaacaattgc tgttaaattt tattaataat      840
attatgatga aatcatataa ggatgcgaag tatttggtta attatggtca tgctggaaag      900
tatagaaatg aacaacgctt ttgggggaga tgtgaacgta aatttaaact tcaaagaatt      960
attgaatatt attctcaatt gtttgataga aaataa                                996
```

```
<210> SEQ ID NO 6
<211> LENGTH: 331
<212> TYPE: PRT
<213> ORGANISM: Bacteroides fragilis

<400> SEQUENCE: 6

Met Cys Asp Cys Leu Ser Ile Ile Leu Leu Val Lys Met Lys Lys Ile
1               5                   10                  15

Tyr Leu Lys Phe Val Asp Phe Trp Asp Gly Phe Asp Thr Ile Ser Asn
            20                  25                  30

Phe Ile Val Asp Ala Leu Ser Ile Gln Tyr Glu Val Val Leu Ser Asn
        35                  40                  45

Glu Pro Asp Tyr Leu Phe Tyr Ser Cys Phe Gly Thr Ser His Leu Glu
    50                  55                  60

Tyr Asp Cys Ile Lys Ile Met Phe Ile Gly Glu Asn Ile Val Pro Asp
65                  70                  75                  80

Phe Asn Val Cys Asp Tyr Ala Ile Gly Phe Asn Tyr Ile Asp Phe Gly
                85                  90                  95

Asp Arg Tyr Leu Arg Leu Pro Leu Tyr Ala Ile Tyr Asp Gly Phe Ser
            100                 105                 110

Asn Leu Gln Asn Lys Lys Ile Asp Val Asn Lys Ala Leu Asp Arg Lys
        115                 120                 125

Phe Cys Ser Ile Val Val Ser Asn Asn Lys Trp Ala Asp Pro Ile Arg
    130                 135                 140

Glu Thr Phe Phe Lys Leu Leu Ser Ser Tyr Lys Lys Val Asp Ser Gly
145                 150                 155                 160

Gly Arg Ala Trp Asn Asn Ile Gly Gly Pro Val Asp Asn Lys Leu Asp
                165                 170                 175

Phe Ile Ser Gln Tyr Lys Phe Asn Ile Ala Phe Glu Asn Ser Arg Val
            180                 185                 190

Leu Gly Tyr Thr Thr Glu Lys Ile Met Glu Pro Met Gln Val Asn Ser
            195                 200                 205

Ile Pro Val Tyr Trp Gly Asn Pro Leu Val Gly Lys Asp Phe Asn Val
    210                 215                 220

Asp Ser Phe Val Asn Ala His Asp Phe Asp Ser Leu Glu Arg Leu Val
225                 230                 235                 240

Glu Tyr Ile Ile Glu Leu Asp Ser Ser Lys Asp Lys Tyr Leu Glu Met
                245                 250                 255
```

-continued

```
Leu Glu Lys Pro Trp Leu Leu Asp Lys Thr Tyr Leu Asp Trp Lys Gln
        260             265             270

Leu Leu Leu Asn Phe Ile Asn Asn Ile Met Met Lys Ser Tyr Lys Asp
        275             280             285

Ala Lys Tyr Leu Val Asn Tyr Gly His Ala Gly Lys Tyr Arg Asn Glu
    290             295             300

Gln Arg Phe Trp Gly Arg Cys Glu Arg Lys Phe Lys Leu Gln Arg Ile
305             310             315             320

Ile Glu Tyr Tyr Ser Gln Leu Phe Asp Arg Lys
            325             330
```

```
<210> SEQ ID NO 7
<211> LENGTH: 264
<212> TYPE: DNA
<213> ORGANISM: Artificial Sequence
<220> FEATURE:
<223> OTHER INFORMATION: Description of the artificial sequence: partial
      base sequence of codon-optimized BfFucT

<400> SEQUENCE: 7
cgtaagttct gcagcatcgt ggttagcaat aataaatggg cggacccgat tcgtgagacc      60
tttttcaaac tgctgagcag ctacaaaaag gtggacagcg gtggccgtgc gtggaacaac     120
atcggtggcc cggttgacaa caagctggat ttcatcagcc agtacaaatt caacattgcg     180
tttgagaaca gccgtgtgct gggttacacc accgaaaaga ttatggagcc gatgcaagtg     240
aacagcattc cggtttactg gggt                                           264
```

```
<210> SEQ ID NO 8
<211> LENGTH: 20
<212> TYPE: DNA
<213> ORGANISM: Artificial Sequence
<220> FEATURE:
<223> OTHER INFORMATION: Description of the artificial sequence: base
      sequence of primer for amplification of cat

<400> SEQUENCE: 8
accaggcgtt taagggcacc                                                 20
```

```
<210> SEQ ID NO 9
<211> LENGTH: 45
<212> TYPE: DNA
<213> ORGANISM: Artificial Sequence
<220> FEATURE:
<223> OTHER INFORMATION: Description of the artificial sequence: base
      sequence of primer for amplification of cat

<400> SEQUENCE: 9
gactacgggc ctaaagtcga cagaataaat aaatcctggt gtccc                     45
```

```
<210> SEQ ID NO 10
<211> LENGTH: 28
<212> TYPE: DNA
<213> ORGANISM: Artificial Sequence
<220> FEATURE:
<223> OTHER INFORMATION: Description of the artificial sequence: base
      sequence of  primer for amplification of sacB

<400> SEQUENCE: 10
gtcgacttta ggcccgtagt ctgcaaat                                        28
```

```
<210> SEQ ID NO 11
<211> LENGTH: 21
<212> TYPE: DNA
```

-continued

```
<213> ORGANISM: Artificial Sequence
<220> FEATURE:
<223> OTHER INFORMATION: Description of the artificial sequence: base
      sequence of  primer for amplification of sacB

<400> SEQUENCE: 11
tacggttagc catttgcctg c                                               21

<210> SEQ ID NO 12
<211> LENGTH: 42
<212> TYPE: DNA
<213> ORGANISM: Artificial Sequence
<220> FEATURE:
<223> OTHER INFORMATION: Description of the artificial sequence: base
      sequence of primer for amplification of lacZ Upstream 1

<400> SEQUENCE: 12
ggtgccctta aacgcctggt agctgtttcc tgtgtgaaat tg                        42

<210> SEQ ID NO 13
<211> LENGTH: 18
<212> TYPE: DNA
<213> ORGANISM: Artificial Sequence
<220> FEATURE:
<223> OTHER INFORMATION: Description of the artificial sequence: base
      sequence of primer for amplification of lacZ Upstream 1

<400> SEQUENCE: 13
ccagtctggc cctgcacg                                                   18

<210> SEQ ID NO 14
<211> LENGTH: 43
<212> TYPE: DNA
<213> ORGANISM: Artificial Sequence
<220> FEATURE:
<223> OTHER INFORMATION: Description of the artificial sequence: base
      sequence of primer for  amplification of lacY Downstream 1

<400> SEQUENCE: 14
gcaggcaaat ggctaaccgt acgaccaaca tatcataacg gag                       43

<210> SEQ ID NO 15
<211> LENGTH: 20
<212> TYPE: DNA
<213> ORGANISM: Artificial Sequence
<220> FEATURE:
<223> OTHER INFORMATION: Description of the artificial sequence: base
      sequence of primer for  amplification of lacY Downstream 1

<400> SEQUENCE: 15
gtttccgctc tgtttgctgc                                                 20

<210> SEQ ID NO 16
<211> LENGTH: 42
<212> TYPE: DNA
<213> ORGANISM: Artificial Sequence
<220> FEATURE:
<223> OTHER INFORMATION: Description of the artificial sequence: base
      sequence of  primer for amplification of  lacZ Upstream 2

<400> SEQUENCE: 16
ccgttatgat atgttggtcg agctgtttcc tgtgtgaaat tg                        42

<210> SEQ ID NO 17
<211> LENGTH: 22
<212> TYPE: DNA
<213> ORGANISM: Artificial Sequence
```

-continued

```
<220> FEATURE:
<223> OTHER INFORMATION: Description of the artificial sequence: base
      sequence of amplification primer for amplification of lacY
      Downstream 2

<400> SEQUENCE: 17
cgaccaacat atcataacgg ag                                            22

<210> SEQ ID NO 18
<211> LENGTH: 41
<212> TYPE: DNA
<213> ORGANISM: Artificial Sequence
<220> FEATURE:
<223> OTHER INFORMATION: Description of the artificial sequence: base
      sequence of primer for amplification of wcaJ Upstream 1

<400> SEQUENCE: 18
ggtgccctta aacgcctggt cgttgttcct gttattagcc c                       41

<210> SEQ ID NO 19
<211> LENGTH: 20
<212> TYPE: DNA
<213> ORGANISM: Artificial Sequence
<220> FEATURE:
<223> OTHER INFORMATION: Description of the artificial sequence: base
      sequence of primer for amplification of wcaJ Upstream 1

<400> SEQUENCE: 19
acgcggtcgc tatcagcaaa                                               20

<210> SEQ ID NO 20
<211> LENGTH: 44
<212> TYPE: DNA
<213> ORGANISM: Artificial Sequence
<220> FEATURE:
<223> OTHER INFORMATION: Description of the artificial sequence: base
      sequence of primer for amplification of wcaM Downstream 1

<400> SEQUENCE: 20
gcaggcaaat ggctaaccgt aatttgcgac cattcctgga aaaa                    44

<210> SEQ ID NO 21
<211> LENGTH: 23
<212> TYPE: DNA
<213> ORGANISM: Artificial Sequence
<220> FEATURE:
<223> OTHER INFORMATION: Description of the artificial sequence: base
      sequence of primer for amplification of wcaM Downstream 1

<400> SEQUENCE: 21
acttcacaaa cgcctgcata tag                                           23

<210> SEQ ID NO 22
<211> LENGTH: 41
<212> TYPE: DNA
<213> ORGANISM: Artificial Sequence
<220> FEATURE:
<223> OTHER INFORMATION: Description of the artificial sequence: base
      sequence of primer for amplification of wcaJ Upstream 2

<400> SEQUENCE: 22
ttccaggaat ggtcgcaaat cgttgttcct gttattagcc c                       41

<210> SEQ ID NO 23
<211> LENGTH: 23
<212> TYPE: DNA
<213> ORGANISM: Artificial Sequence
```

-continued

```
<220> FEATURE:
<223> OTHER INFORMATION: Description of the artificial sequence: base
      sequence of primer for amplification of wcaM Downstream 2

<400> SEQUENCE: 23
atttgcgacc attcctggaa aaa                                            23

<210> SEQ ID NO 24
<211> LENGTH: 26
<212> TYPE: DNA
<213> ORGANISM: Artificial Sequence
<220> FEATURE:
<223> OTHER INFORMATION: Description of the artificial sequence: base
      sequence of primer for amplification of rcsA

<400> SEQUENCE: 24
atgtcaacga ttattatgga tttatg                                         26

<210> SEQ ID NO 25
<211> LENGTH: 42
<212> TYPE: DNA
<213> ORGANISM: Artificial Sequence
<220> FEATURE:
<223> OTHER INFORMATION: Description of the artificial sequence: base
      sequence of primer for amplification of rcsA

<400> SEQUENCE: 25
cattctagac ctccttaatt agcgcatgtt gacaaaaata cc                       42

<210> SEQ ID NO 26
<211> LENGTH: 36
<212> TYPE: DNA
<213> ORGANISM: Artificial Sequence
<220> FEATURE:
<223> OTHER INFORMATION: Description of the artificial sequence: base
      sequence of primer for amplification of bffucT

<400> SEQUENCE: 26
aggaggtcta gaatgtgtga ttgcttgtct atcata                              36

<210> SEQ ID NO 27
<211> LENGTH: 38
<212> TYPE: DNA
<213> ORGANISM: Artificial Sequence
<220> FEATURE:
<223> OTHER INFORMATION: Description of the artificial sequence: base
      sequence of primer for amplification of bffucT

<400> SEQUENCE: 27
ggatttcctc tcgagttatt ttctatcaaa caattgag                            38

<210> SEQ ID NO 28
<211> LENGTH: 38
<212> TYPE: DNA
<213> ORGANISM: Artificial Sequence
<220> FEATURE:
<223> OTHER INFORMATION: Description of the artificial sequence: base
      sequence of primer for amplification of brfucT

<400> SEQUENCE: 28
aggaggtcta gaatgaaatt gaaagtgaaa tttgtaga                            38

<210> SEQ ID NO 29
<211> LENGTH: 35
<212> TYPE: DNA
<213> ORGANISM: Artificial Sequence
<220> FEATURE:
```

<223> OTHER INFORMATION: Description of the artificial sequence: base
      sequence of primer for amplification of brfucT

<400> SEQUENCE: 29
ggatttcctc tcgagtcatc taaaccaacg acaag                                35

<210> SEQ ID NO 30
<211> LENGTH: 22
<212> TYPE: DNA
<213> ORGANISM: Artificial Sequence
<220> FEATURE:
<223> OTHER INFORMATION: Description of the artificial sequence: base
      sequence of primer for amplification of cBrFucT Upstream

<400> SEQUENCE: 30
attcagagct tcctgtgaat ta                                              22

<210> SEQ ID NO 31
<211> LENGTH: 41
<212> TYPE: DNA
<213> ORGANISM: Artificial Sequence
<220> FEATURE:
<223> OTHER INFORMATION: Description of the artificial sequence: base
      sequence of primer for amplification of cBrFucT Midstream

<400> SEQUENCE: 31
attcacagga agctctgaat cgtaagttct gcagcatcgt g                         41

<210> SEQ ID NO 32
<211> LENGTH: 20
<212> TYPE: DNA
<213> ORGANISM: Artificial Sequence
<220> FEATURE:
<223> OTHER INFORMATION: Description of the artificial sequence: base
      sequence of primer for amplification of cBrFucT Midstream

<400> SEQUENCE: 32
accccagtaa accggaatgc                                                 20

<210> SEQ ID NO 33
<211> LENGTH: 40
<212> TYPE: DNA
<213> ORGANISM: Artificial Sequence
<220> FEATURE:
<223> OTHER INFORMATION: Description of the artificial sequence: base
      sequence of primer for amplification of cBrFucT Downstream

<400> SEQUENCE: 33
gcattccggt ttactggggt aacagattgg ttgagttgga                           40

<210> SEQ ID NO 34
<211> LENGTH: 45
<212> TYPE: DNA
<213> ORGANISM: Artificial Sequence
<220> FEATURE:
<223> OTHER INFORMATION: Description of the artificial sequence: base
      sequence of primer for amplification of lacY

<400> SEQUENCE: 34
ctcgagagga aatccattat gtactattta aaaaacacaa acttt                     45

<210> SEQ ID NO 35
<211> LENGTH: 23
<212> TYPE: DNA
<213> ORGANISM: Artificial Sequence
<220> FEATURE:
<223> OTHER INFORMATION: Description of the artificial sequence: base -continued

```
         sequence of primer for amplification of lacY

<400> SEQUENCE: 35
ttaagcgact tcattcacct gac                                          23

<210> SEQ ID NO 36
<211> LENGTH: 41
<212> TYPE: DNA
<213> ORGANISM: Artificial Sequence
<220> FEATURE:
<223> OTHER INFORMATION: Description of the artificial sequence: base
         sequence of primer for amplification of rcsA-cBrFucT-lacY

<400> SEQUENCE: 36
gaggagaaat taaccatgtc aacgattatt atggatttat g                      41

<210> SEQ ID NO 37
<211> LENGTH: 38
<212> TYPE: DNA
<213> ORGANISM: Artificial Sequence
<220> FEATURE:
<223> OTHER INFORMATION: Description of the artificial sequence: base
         sequence of primer for amplification of rcsA-cBrFucT-lacY

<400> SEQUENCE: 37
agggcatcgg tcgacttaag cgacttcatt cacctgac                          38

<210> SEQ ID NO 38
<211> LENGTH: 21
<212> TYPE: DNA
<213> ORGANISM: Artificial Sequence
<220> FEATURE:
<223> OTHER INFORMATION: Description of the artificial sequence: base
         sequence of primer for amplification of pPE167

<400> SEQUENCE: 38
gtcgaccgat gcccttgaga g                                            21

<210> SEQ ID NO 39
<211> LENGTH: 25
<212> TYPE: DNA
<213> ORGANISM: Artificial Sequence
<220> FEATURE:
<223> OTHER INFORMATION: Description of the artificial sequence: base
         sequence of primer for amplification of pPE167

<400> SEQUENCE: 39
ggttaatttc tcctctttaa tatcg                                        25
```